United States Patent [19]

Eyrick et al.

[11] 4,096,858
[45] Jun. 27, 1978

[54] VOLUME-RATE RESPIRATOR SYSTEM AND METHOD

[75] Inventors: Theodore B. Eyrick, Reading; Allen C. Brown, Acton; Neil R. Hattes, Danvers, all of Mass.

[73] Assignee: Chemetron Corporation, Chicago, Ill.

[21] Appl. No.: 752,753

[22] Filed: Dec. 20, 1976

Related U.S. Application Data

[62] Division of Ser. No. 545,287, Jan. 29, 1975, which is a division of Ser. No. 402,677, Oct. 2, 1973.

[51] Int. Cl.² ............................................. A61M 16/00
[52] U.S. Cl. .................................................. 128/145.6
[58] Field of Search ........................ 128/145.5–145.8, 128/142.3; 417/328, 395, 472, 473, 326; 185/27

[56] References Cited

U.S. PATENT DOCUMENTS

| 862,867 | 8/1907 | Eggleston | 417/395 |
|---|---|---|---|
| 2,828,694 | 4/1958 | Nallinger | 417/328 |
| 3,307,542 | 3/1967 | Andreasen | 128/145.8 |
| 3,598,505 | 8/1971 | Greene | 417/473 |
| 3,754,550 | 8/1973 | Kipling | 128/145.8 |

*Primary Examiner*—Robert W. Michell
*Assistant Examiner*—Henry J. Recla
*Attorney, Agent, or Firm*—Jones, Tullar & Cooper; Nicholas M. Esser

[57] ABSTRACT

A respiration unit for supplying a preselected limited volume of breathing gas to a patient at limited positive pressures, and at a preselected limited flow rate is disclosed. The system includes an air delivery cylinder having a drive weight which is free to move up and down. A diaphragm connected to the weight divides the cylinder into an upper control chamber and a lower delivery chamber. A vacuum source is connected to the control chamber through a first solenoid-controlled valve to regulate the lifting of the weight, and a second solenoid-controlled valve regulates the bleeding of air into the control chamber to release and regulate the rate of fall of the weight, thereby driving breathing gas under pressure out of the lower chamber. A control system regulates the lift and lower cycles of the drive weight to provide the required operation of the system, with various sensors being provided to allow patient control of the system under selected conditions, and to assure patient safety.

The control system incorporates, among other things, means for providing a variable inspiratory-expiratory ratio, for permitting patient assisted breathing, for mixing oxygen with air or anesthetic gases, for periodically altering the breathing pattern, for permitting selection of positive or negative end expiratory pressure, for allowing selection of the breathing waveform, and for providing accurate displays of essential parameters.

7 Claims, 19 Drawing Figures

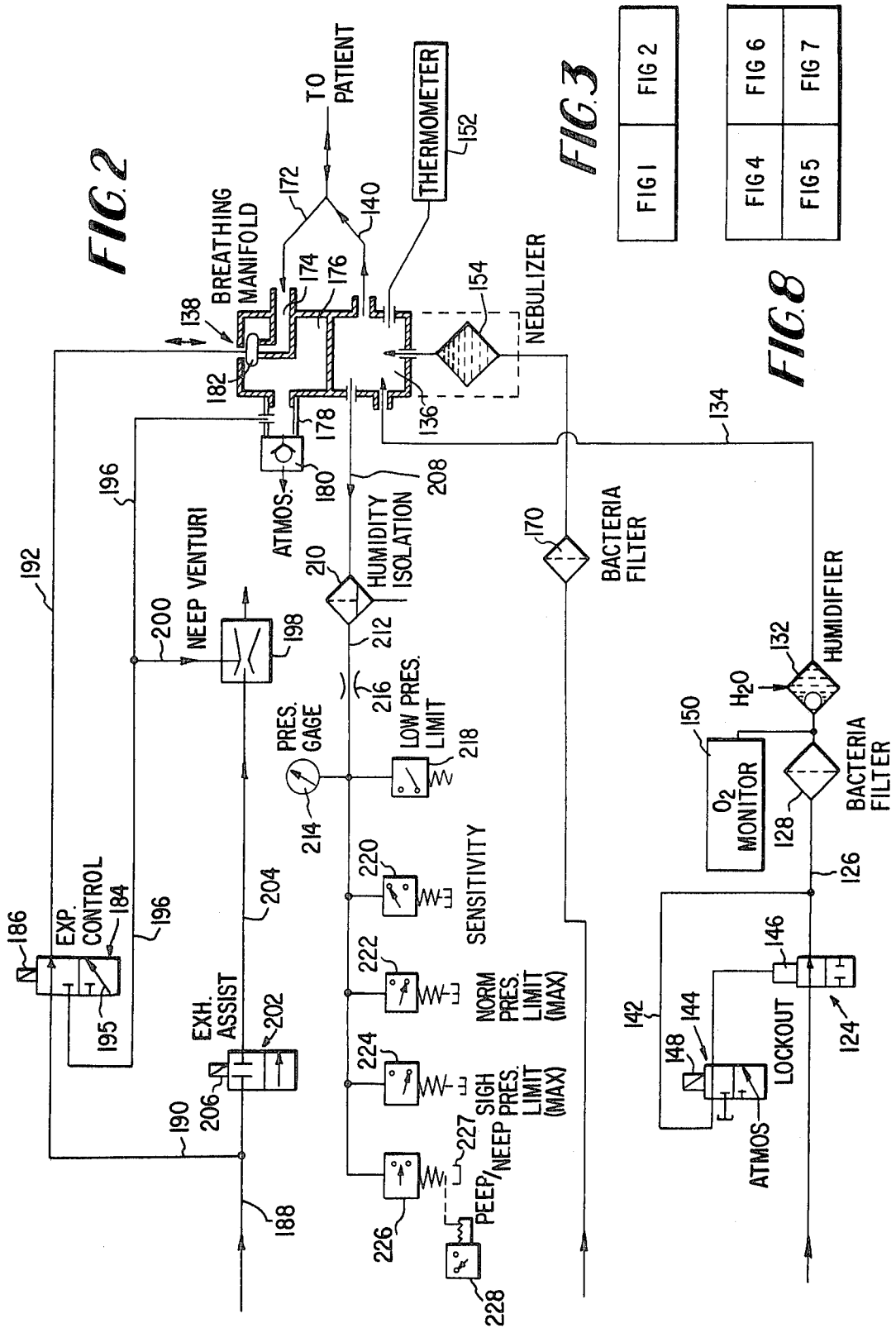

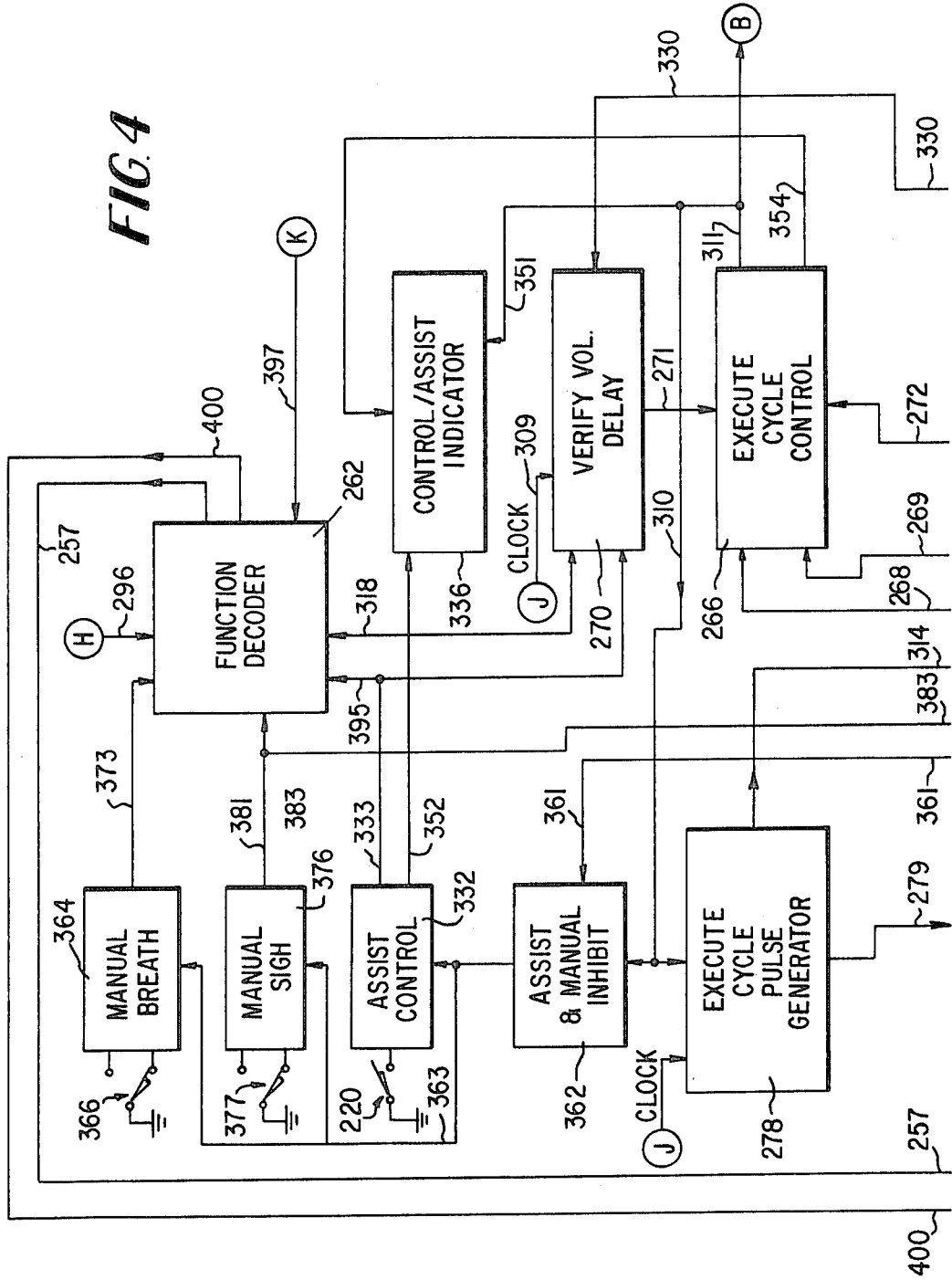

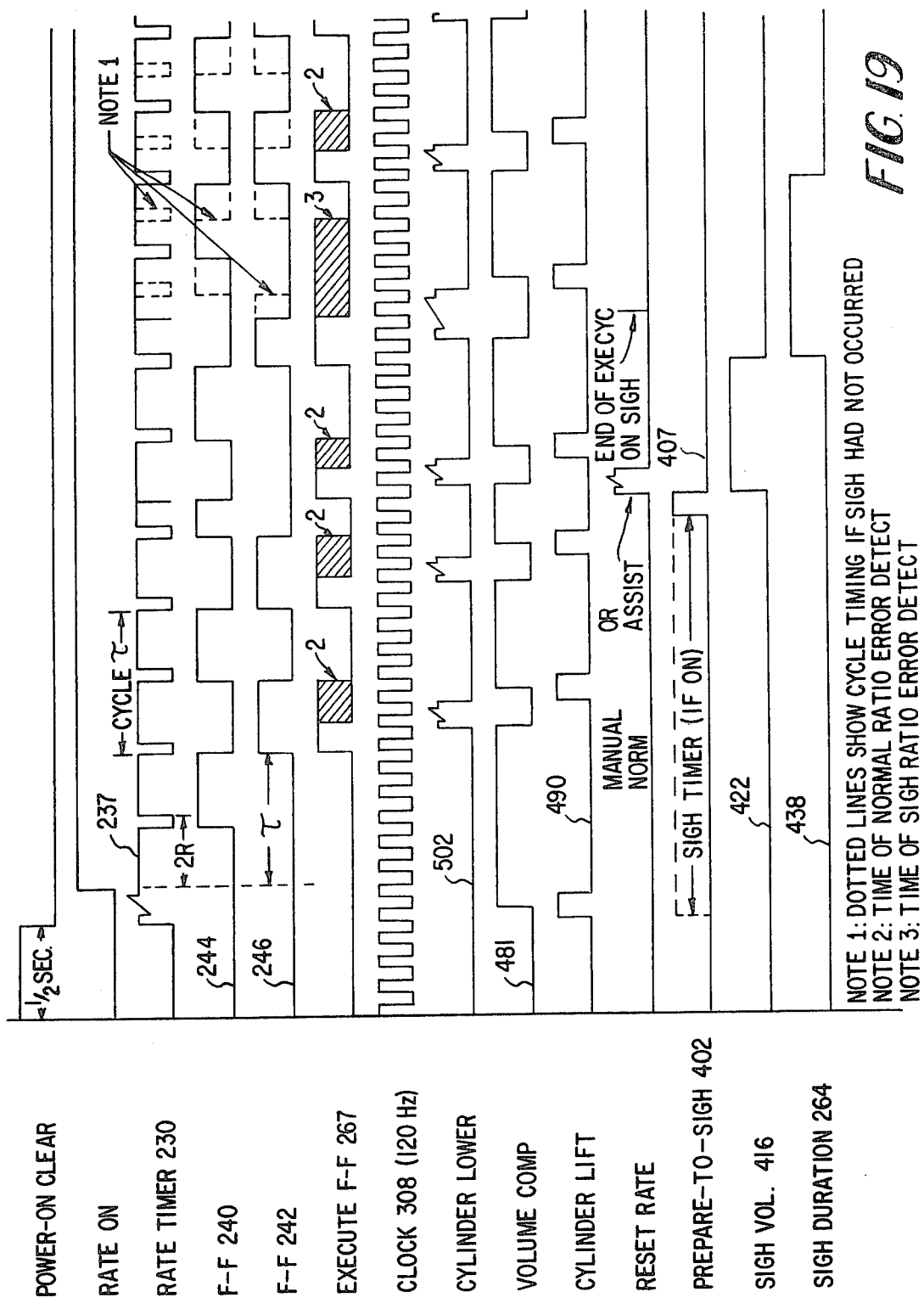

VOLUME-RATE RESPIRATOR SYSTEM AND METHOD

This application is a division of application Ser. No. 545,287, filed Jan. 29, 1975, which is in turn a division of application Ser. No. 402,677, filed Oct. 2, 1973, and which issued on Sept. 16, 1975 as U.S. Pat. No. 3,905,362.

BACKGROUND OF THE INVENTION

The present invention relates, in general, to respiration systems, and more particularly to such a system which inherently provides a safe, reliable operation and which is easily controlled, highly flexible, and capable of a great variety of operational modes which permit a wide choice of functions for maximum effectiveness in use.

This application is related to copending application Ser. No. 402,679, of Theodore B. Eyrick and Allen C. Brown, filed on even date herewith and entitled "Breathing Gas Delivery Cylinder for Respirators", now U.S. Pat. No. 3,932,066, and application Ser. No. 402,678, of Theodore B. Eyrick and Neil R. Hattes, filed on even date herewith and entitled "Respiration Ratemeter", now U.S. Pat. No. 3,887,795, the disclosures of which are hereby incorporated herein.

Numerous types of respiration devices and systems have been developed in the prior art, and have at one time or another been on the market. Such systems have all generally had characteristics and features which met special needs or which overcame specific problems, and thus were of value to the art in specific circumstances. But, unfortunately, many of the prior art systems had flaws which made them inappropriate for use in some cases, or which made them unreliable, difficult to control, or inaccurate, and thus the search has continued for an improved respirator which would overcome such difficulties.

The basic types of respirators are well known, having been in clinical use for many years and often discussed, both as to advantages and shortcomings, in the technical literature. Some of the respirators now in use are described by W. W. Mushin, L. Rendell-Baker, P. W. Thompson and W. W. Mapleson in their book *Automatic Ventilation of the Lungs,* 2nd, Ed., F. A. Davis Co., Philadelphia, Pa. (1969), and by W. T. Heironimus in *Mechanical Artificial Ventilation,* C. C. Thomas, Springfield, Illinois (1967), as well as in other publications.

Broadly speaking, respirator devices can be classified by the parameter which controls the cycling of the machine: pressure, time, or volume of gas, and many currently available machines can be so classified. A pressure-cycling machine allows air to be delivered to a patient until a preset pressure is reached, at which time the control system closes the valve controlling air flow. A disadvantage of the pressure-cycled machine is that it will deliver varying quantities (tidal volumes) of air when the pulmonary back pressure or the compliance of the system changes. This requires that the ventilation be very closely monitored to insure that the gas level of the blood does not fall outside desired limits. Generally, too, such systems have relatively low pressure capabilities and present problems in controlling the amount of oxygen delivered to the patient.

A time-cycled machine sets the time for inspiration and expiration, so that the volume of air actually delivered becomes a function of flow rate. Since the flow is limited by pulmonary resistance, changes in this factor leads to variations in the volume delivered. Most such systems also have relatively low peak pressures.

Volume-controlled machines provide a relatively constant tidal volume delivery, except, under very high pulmonary resistance conditions, where losses due to the compressibility of the gas becomes a factor. These devices generally have high pressure and flow capability, but may be limited in the particular features made available in a given machine. Although volume-controlled machines provide the advantage of delivering a desired quantity of air on each cycle, the utilization of this concept has not been without problems in prior art machines. For example, in a volume-controlled machine it is essential that the measurement of volume be very accurate to insure that the machine functions properly. However, prior machines have not been reliable in this regard, and because of compliance in the machine itself, difficulties in obtaining an accurate determination of the location of a movable piston or like air drive mechanism, and sluggish mechanical or electrical control systems, it has not been possible to provide a volume system that would repeatedly provide a selected quantity of air for a patient.

Another difficulty encountered with volume-controlled systems is the likelihood of encountering excessive pressures, and such systems thus can produce a considerable safety problem. Where a gas delivery machine is arranged to sense and be controlled by the volume of gas being delivered, high pressures can appear, and it then becomes necessary to provide often complex sensing and control systems to guard against injuring the patient. However, the fact that dangerous pressures can be produced is a safety hazard in itself, for failure of the control system can result in damage. For example, pressure relief valves are commonly used in such systems to regulate the maximum pressure that can exist; but the operational characteristics of such valves can change over a period of time, and if one should fail at the wrong time, a patient could be injured.

In a volume system, it is common to provide a bellows or other air container which will receive the gas to be delivered to the patient. The container is then compressed mechanically or pneumatically to discharge the air to the patient when the inhalation portion of a breathing cycle is reached. In such systems it is customary to fill the container to its maximum volume prior to inhalation, and to then terminate the discharge when the desired volume has been delivered. A real danger exists with this arrangement, however, for if the control system should fail during the discharge stroke, the full volume of air the machine is capable of delivering can be discharged into the patient's lungs, and can do irreparable harm.

A volume controlled system which relies on sensing the delivered volume and controlling the end point of the delivery stroke may also be inaccurate because of the overshoot that will occur after the stop signal has been given. Inertia within the mechanical delivery apparatus and lost motion in the controls may result in the mechanism moving past the desired stop point, and this can produce an inaccuracy in the delivery of the breathing gas.

In general, then, it can be said that although prior respirator or ventilator devices have been satisfactory, nevertheless, they have been too inflexible and have not been capable of safely meeting the needs of various patients in various circumstances. A patient whose breathing must be completely controlled, for example, requires different machine characteristics than a patient whose breathing is merely being machine assisted. Often a patient whose breathing has been machine controlled for an extended period becomes dependent upon the machine, and cannot breathe without it. Such a patient must be gradually withdrawn from the machine, and thus flexibility in operation to allow shifting from machine to patient controlled breathing is highly desirable. A machine that does not have flexibility and reliability, then, cannot meet the varying needs of patients.

SUMMARY OF THE INVENTION

It is, therefore, an object of the present invention to provide a respirator unit which is flexible, reliable, easily controlled, and, above all, safe.

It is a further object of the invention to provide a respirator system which is easy to use, compact, and accurate, and which provides a variety of features to enable safe and convenient delivery of breathing gas to a patient.

In accordance with a preferred embodiment of the present invention, a respirator system is provided which is mechanically arranged and electrically controlled to produce an accurate and repeatable delivery of a preselected limited volume of breathing gas to a patient at limited positive pressures and at preselected limited flow rates. The system responds to a variety of sensed parameters to regulate the respirator apparatus and provide total and adjustable control of the breathing gas supplied to a patient, in accordance with the desires of the operator. This is accomplished through an air delivery unit which comprises a vertically positioned cylindrical housing containing an axially extending hollow shaft which forms a guide for a movable weight that is mounted, by means of suitable bearings, on the shaft. A follower chain extends through the hollow central shaft and is attached to the weight and to an external potentiometer, whereby motion of the weight within the housing causes a corresponding variation in the output of the potentiometer to provide an indication of the exact position of the weight within the cylinder. A rolling diaphragm seals the circumference of the sliding weight to the inner surface of the cylindrical housing into an upper and lower chamber. The chambers are sealed from the central shaft by means of upper and lower bellows which surround the shaft and are secured between the sliding weight and the upper and lower ends of the housing.

A vacuum pump is connected to the upper chamber through a solenoid-operated control valve, while the lower chamber is opened through an inlet check valve to a supply of breathing gas and through an outlet check valve to the patient's lungs, the valves serving to insure the proper direction of flow. Application of a vacuum to the upper chamber allows the breathing gas, which is at approximately atmospheric pressure, to enter the lower chamber and lift the sliding weight upwardly to a preselected position, the breathing gas filling the expanding lower chamber. The location of the weight is monitored by the potentiometer so that when it approaches the desired level, corresponding to a desired volume of gas in the lower chamber, the vacuum control valve can be closed. The breathing gas may be atmospheric air, oxygen, an anesthetic breathing gas mixture, or a combination of these in accordance with the needs of the patient.

Also connected to the upper chamber is a bleeder valve which is variable to allow the vacuum in the upper chamber to be relieved at a predetermined maximum rate. This allows the weight to move downwardly under the force of gravity to compress the lower chamber and force breathing gas out of its outlet at a rate limited by the setting of the bleeder valve, and by the back pressure produced in the lower chamber.

The raising and lowering of the movable weight within the cylinder, and the consequent expanding and contracting of the lower chamber, produces a periodic flow of air from the chamber through suitable conduits, filters, humidifiers, and the like to a conventional breathing manifold, which may be connected to a mask or inserted tube, for supplying breathing gas to a patient in accordance with a preselected, adjustable breathing cycle. As soon as the cylinder has completed the delivery of gas, the weight is lifted to the preselected volume location in readiness for the next breathing cycle, and is held in that location until the control system calls for the delivery of air.

As is known, a breathing cycle includes an inspiration mode, or phase, when the patient inhales or is caused to inhale by the respirator, an expiration mode, when the patient exhales, and an inflation hold mode, which occurs between inspiration and expiration, when the patient is in effect holding his breath. The time relationship of these three modes may be referred to as the breath waveform, and in the present system this waveform may be adjusted to provide the required breathing pattern for the patient. In the inspiration mode, which is at the start of a breathing cycle, the cylinder is operated to deliver breathing gas at a rate, volume, and pressure that is determined by the breath waveform and the setting of the machine controls. During the hold and exhalation modes, the cylinder drive weight returns to its upper position and a check valve is closed to prevent exhaled gas from returning to the cylinder. Following the end of the hold mode, if any, the exhalation mode occurs when an expiration path is opened through the conventional breathing manifold to atmosphere. During the exhalation mode, if it is desired to assist the patient to exhale, or if it is desired to produce a negative end expiratory pressure (neep), a flow of air is generated through a venturi arrangement which then serves to draw air out of the patient's lungs. When a positive end expiratory pressure (peep) is desired during the exhalation mode, the expiration balloon valve within the conventional breathing manifold is cycled to maintain the preselected level of positive end expiratory pressure.

The system is controlled by a circuit which effects the energization of the various solenoid-operated valves in accordance with the condition of the patient, of the respirator itself, or in accordance with the values of adjustable controls and sensors. Several of these adjustable controls and sensors are photosensors which respond to the system pressure at predetermined locations to operate the solenoids in accordance with a preset pattern or in response to emergency conditions. Thus, although the system is operable on a fully controlled basis, wherein the patient plays a passive role and the machine produces the necessary inspiratory and expiratory breathing patterns, it is also operable on a patient demand basis, wherein activity by the patient in attempting to breath on his own overrides the preset rate control. The activity of the patient in trying to inhale during an expiratory mode, for example, may be sensed as a change in pressure within the breathing manifold;

and this change may be used to override the preset rate pattern and allow the patient to inhale before completion of the programmed exhalation. The degree of patient activity required to override the system operation may be preset by a sensitivity control which may be adjusted to provide the override at a selected pressure level. Other sensors detect low and high pressures within the system to insure proper cycling, and established limits to provide an extra measure of patient safety. Various manual overrides are also available in the system to permit the operator to initiate a breathing cycle, or to produce a sigh, at any time in place of the automatically recurring breathing and sigh cycles provided by the system. Various other automatic and manual controls will become apparent from the more detailed description which follows.

The operation of the system is carried out by means of a logic circuit which responds to the various sensors and control switches to provided output signals which serve to activate or deactivate corresponding solenoid valves, indicator lights, alarms, and the like. The logic control circuitry of the system may be roughly divided into three general functions; basic control, power, and alarm and volume control. The basic control circuit regulates the normal cycling rate of the machine and the aborting of a cycle in response to an alarm or an override caused by patient demand. The control also responds to an exhale assist signal and permits manual as well as automatic regulation of normal and sigh cycles. The normal cycling of the machine is under the control of an astable multivibrator within a normal rate control circuit which initiates the inspiratory mode of the machine at preset intervals to start the successive machine cycles. The output pulses from the normal rate control energize a pulse generator to create an execute cycle pulse which is used in conjunction with the rate control signal to operate the system in accordance with the predetermined parameters. The operation of the breathing cycle, which includes the inhale, hold, and exhale modes, is automatic, unless overridden in response to monitored conditions, whereby a positive control of the breathing cycle and of the inspiration-expiration ratio is provided.

The power control circuitry responds to the control signals to drive the solenoid-controlled valves, provides a clearing signal for clearing the logic circuitry immediately following the start up of the system upon initial application of power, provides machine synchronization, monitors power failures and powers the audible and visual alarms for the system.

The alarm and volume control circuitry in the preferred embodiment of this system monitors such machine conditions as proper cycling of the gas delivery cylinder to insure that the full volume is being delivered, oxygen ratio in the breathing gas, pressure limits within the system, and compares the volume control setting of the machine with the rest position of the gas delivery drive weight at the end of its upstroke. This circuit portion also provides condition indicators, and incorporates a ratemeter for responding to successive inhalations to provide a continuous breathing rate indication.

A respirator system thus constructed overcomes many difficulties encountered with prior art systems and provides a highly accurate, repeatable delivery of preselected volumes of breathing gases at preselected rates, with a high degree of safety. Because of the use of a delivery cylinder having a rolling diaphragm arrangement separating an upper control chamber from a lower delivery chamber, a delivery chamber having a very low compliance is provided, thereby permitting accurate control of the volume of the gas being delivered to the patient, and permitting limitation of the pressure within close tolerances.

The use of a sliding weight to provide the driving force on the delivery stroke of the cylinder produces a distinct improvement over prior devices in that the air delivery system does not rely on complex control systems to protect the patient. This is due to the fact that the maximum pressure that can be generated in the delivery chamber under any condition is that produced by the force of gravity acting on the weight. By selecting this weight, in the design of the cylinder, to have a mass which will produce a maximum pressure within known limits even under free falling, or no-control, conditions, the system may be made self-pressure limiting, thereby providing a large margin of safety for the patient. Again, because it is the operation of the moving weight under the influence of gravity, but restricted by the bleeder valve, that produces the outward flow of gas to the patient, the cylinder is limited as to the maximum rate of flow that can be produced, thereby further improving patient safety with fewer components than are required in prior art systems.

Since the weight remains constant as it moves down the central shaft of the cylinder during the delivery stroke, the flow of gas to the patient is unaffected by cylinder compliance and other variations that occurred in prior art systems. Furthermore, the moving weight arrangement of this invention provides a simple, highly accurate, repeatable method of selecting and delivering a desired volume of breathing gas. By regulating the position taken by the weight at the end of its upward, or loading stroke, the volume of breathing gas drawn into the delivery chamber is accurately known, because of the low compliance of the chamber. Further, the location of the weight, and thus the volume of the delivery chamber, is monitored prior to the delivery stroke so that if an error has occurred in the control system it can be recognized before the delivery portion of the cycle begins. Because the delivery stroke always ends adjacent to the bottom of the cylinder, discharging virtually all the air stored in the delivery chamber, only the preselected volume can be delivered.

BRIEF DESCRIPTION OF THE DRAWINGS

The foregoing and additional objects, features, and advantages of the invention will be more fully appreciated when considered in the light of the following detailed description of a preferred embodiment thereof, selected for purposes of illustration and shown in the accompanying drawings, in which:

FIGS. 1 and 2 provide a diagramatic illustration of the respirator system of the present invention, including the air delivery cylinder and accompanying pneumatic controls;

FIG. 3 illustrates the relationship of FIGS. 1 and 2;

FIGS. 4 through 7 provide a functional block diagram of a preferred control arrangement for the respirator system of FIGS. 1 and 2;

FIG. 8 illustrates the relationship of FIGS. 4–7;

FIG. 18 illustrates the relationship of FIGS. 9–17, and

FIG. 19 is a system timing diagram.

DESCRIPTION OF A PREFERRED EMBODIMENT

Figure 1:
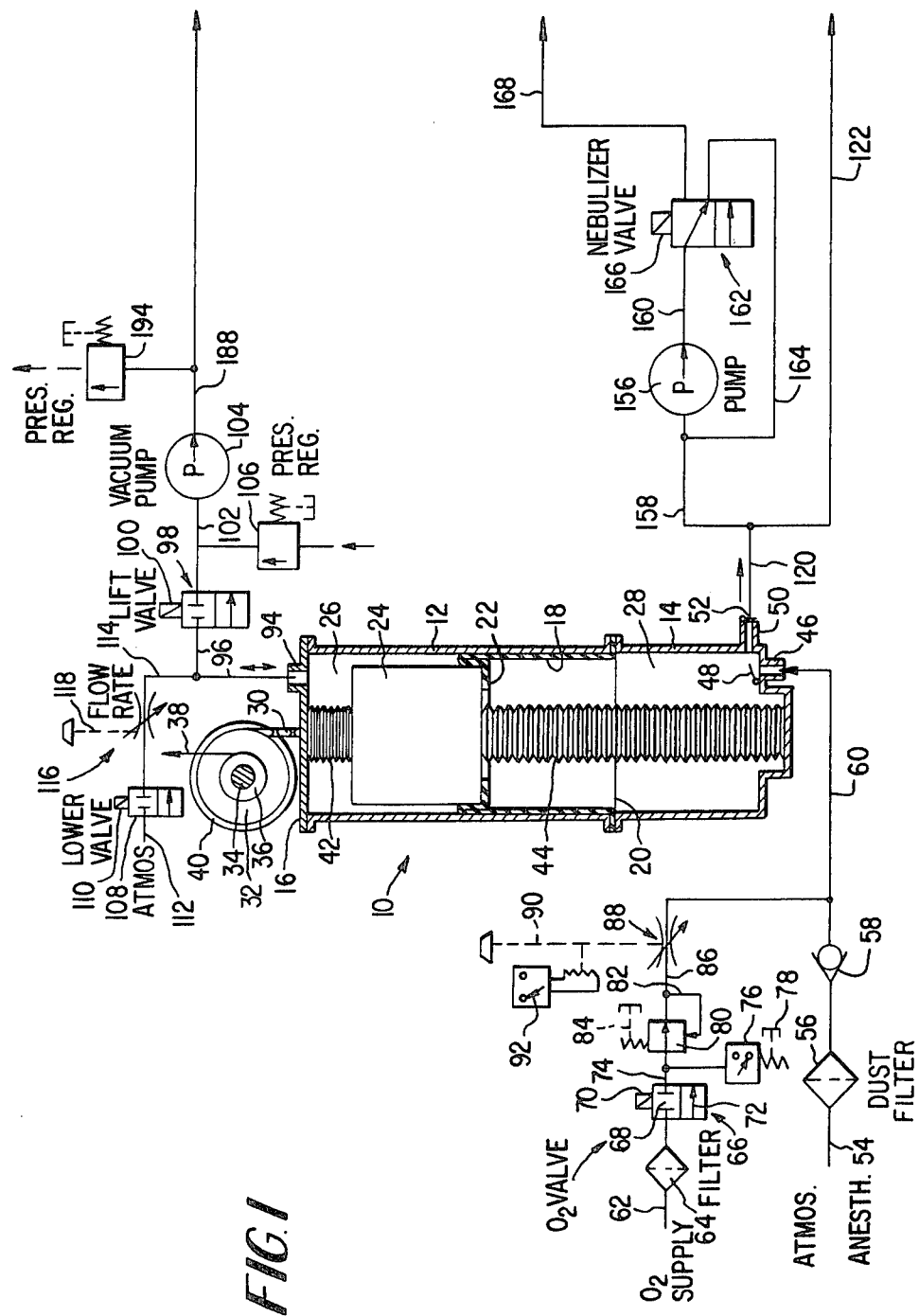
Figure 5:
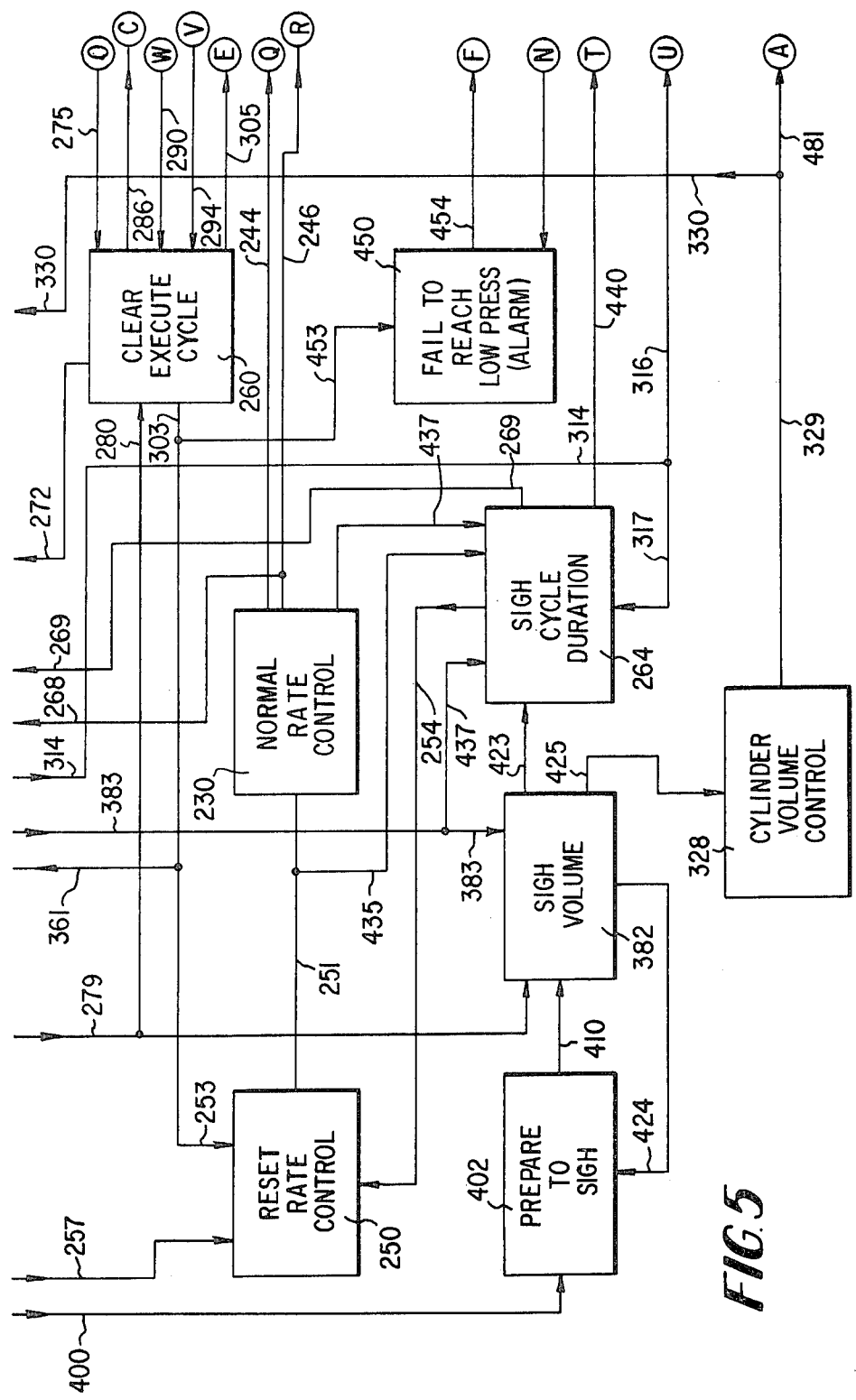

Turning first to a consideration of the pneumatic portion of the respirator system of the present invention, there is illustrated at 10 a gas delivery cyclinder for use in delivering accurate volumes of breathing gas at limited flow rates and pressures, and more particularly for delivering at limited positive pressures a limited volume of gas at a limited flow rate. The delivery cylinder is formed from an upper housing portion 12 which is closed at its lower end by a housing portion 14 and at its upper end by a cap 16. Flanges are formed on adjacent ends of the housing portions, whereby the housing may be clamped or otherwise secured together to form a substantially air tight container. A generally annular rolling diaphragm 18 is secured to the inner wall of the housing and may conveniently be clamped between the contiguous flanges of the housing portions 12 and 14, whereby the outer peripheral edge 20 of the diaphragm forms a gasket between the housing portions.

The inner peripheral edge 22 of the diaphragm is secured to a drive weight 24 which is mounted for vertical sliding motion within cylinder 10. Preferably, the diaphragm is secured to the bottom surface of weight 24, thereby dividing the cylinder into upper and lower chambers 26 and 18, respectively. The weight is freely movable within the cylinder, and is so dimensioned that the rolling diaphragm may be accomodated between the outer peripheral surface of the weight and the inner surface of the housing, whereby the weight may move the full length of the housing with the diaphragm rolling upwardly along inner wall of housing portion 12 when the weight moves toward the top of cylinder 10, and rolling upwardly along the outer peripheral wall of the weight 24 as the weight moves downwardly in the cylinder.

In a preferred form of the invention, the cylinder is provided with an axially located hollow guide shaft which opens through the top and bottom ends of the cylinder. The weight 24 is annular in shape and surrounds the guide shaft, with bearings being provided at the inner surface of the weight to facilitate upward and downward motion. The openings through the ends of the cylinder are provided to admit a follower chain 30 which is secured to weight 24, as by means of a pin connection extending through a slot in the central guide tube, whereby the chain will move with the weight to provide a mechanical connection to indicators located exteriorly of the cylinder. The chain accurately follows the motion of the weight and may, therefore, be used to provide control signals corresponding to the weight location. As indicated in the drawing, follower chain 30 may be connected to a suitable pulley 32 to convert the linear motion of the weight to a rotational motion about a shaft 34. A second indicator pulley 36 may be mounted on shaft 34 to provide a mechanical connection by way of cable 38 to a suitable display device which produces a continuous mechanical indication of the motion and location of weight 24. Since the gas delivery cylinder 10 is of low compliance, by reason of the use of a rolling diaphragm among other things, the position indication provided by cable 38 may be calibrated to provide a direct reading of the volume of chamber 28.

Also mounted on shaft 34 for rotation by follower chain 30 is a potentiometer 40 which provides a resistance reading that will vary linearly with the vertical motion of weight 24, thereby providing an electrical output signal which will vary in accordance with the volume of chamber 28.

Because of the slot formed in the central guide shaft for use in providing a mechanical follower connection, upper and lower bellows 42 and 44, respectively, surround the guide shaft to isolate it from the interior chambers 26 and 28. These bellows are constructed of material, suitably reinforced, that provides them with a substantial memory so that they always assume substantially the same shape upon extension. This memory assists in producing a low compliance in chamber 28, whereby the chamber will always have a known volume for any position of weight 24. Suitable recesses are provided in the cylinder so that the bellows can collapse virtually completely on the upward and downward strokes of the drive weight so that when the weight 24 moves downwardly and approaches the bottom of the cylinder, it will compress bellows 44, thereby providing a minimum of dead space within the cylinder.

The cylinder preferred for use in the present invention is more fully described and illustrated in the co-pending U.S. Pat. No. 3,932,066 referenced above, which is assigned to the assignee of the present application, and reference is made thereto for a more complete description of cylinder 10.

The lower chamber 28 of cylinder 10 is provided with an inlet 46 having a check valve 48, and an outlet 50 having a corresponding check valve 52 for regulating the flow of gas into and out of the chamber. When weight 24 is moved upwardly in cylinder 10, breathing gases are drawn by way of inlet 46 and check valve 48 into the lower chamber 28; when weight 24 moves downwardly, breathing gases within chamber 28 are discharged by way of outlet 50 and check valve 52. Thus, chamber 28 serves as a gas storage and delivery container and operates to deliver gas to a patient during an inspiratory breathing mode.

In the present system, atmospheric air, a combination of air and oxygen, or an anesthetic breathing gas mixture, is to be supplied to chamber 28 for subsequent delivery to a patient whose breathing is to be controlled, assisted, or both. Air or an anesthetic gas mixture is drawn into the system by way of conduit 54, dust filter 56, check valve 58 and an inlet conduit 60 which leads to and is secured on the inlet 46.

When it is desired to enrich the breathing gas being supplied to the patient with oxygen, that gas may be supplied from a suitable source by way of conduit 62, dust filter 64, and a solenoid-operated valve diagrammatically illustrated at 66. This valve is normally closed to the flow of gas, as illustrated by the break 68 in the oxygen supply line. When the solenoid 70 which operates the valve is energized, the valve shifts and is open to gas flow as illustrated by the valve section 72.

All of the solenoid-operated valves used in the present system are diagrammatically illustrated in FIGS. 1 and 2, and as shown each has two conditions, or states, which are illustrated in block form. The illustration for each valve shows two blocks, one representing the valve function in its deactivated state, and the other in its activated state. All of the valves are shown deactivated, and each will be shifted to its other condition upon energization of its associated solenoid. Hereafter, reference to a "closed" valve will refer to a valve that is closed to flow to prevent the passage of fluid, as with section 68 of valve 66. Similarly, reference to an "open" valve will be taken to mean a valve that is open to free flow, and permits the passage of fluid, as indicated by the section 72 of valve 66.

It will be apparent from a consideration of valve 66, that in the deenergized condition illustrated the valve is closed, and no oxygen can be supplied to the air delivery container 10. However, if oxygen is to be added to the air being supplied to cylinder 10, energization of solenoid 70 will shift the valve 66 to its activated condition, allowing oxygen to flow through the path indicated by arrow 72.

Oxygen passing through valve 66 is supplied by way of conduit 74 to a pressure sensing switch 76 having an adjustment 78 for setting the pressure level at which this switch is to operate. This switch senses the inlet oxygen pressure, and normally will be set to sound an alarm whenever the pressure in conduit 74 drops below 30 psi(2.12 kg/cm$^2$).

Pressure sensing switch 76 may be of a conventional type which provides a movable bellows, diaphragm, or the like that responds to varying pressures to make or break a pair of electrical contacts which are adjustably spaced in accordance with the desired closure, or "make", pressure. Thus, when the selected pressure is reached, the sensor switch produces an electrical output that can be used to activate suitable alarm and or control circuitry. Other pressure sensing switches used in this system may be of the same type, although such other switches preferably will be modified versions which utilize conventional gauges having indicator needles. Adjustably positioned along the path of the needle in such switches, and on either side thereof are a photoelectric cell and light source which define an optical path. This photocell arrangement is adjusted to the desired pressure level, and when that pressure is sensed by the pressure gauge, the indicator needle passes between the photocell and light source, interrupting the optical path and producing an electrical signal which may be utilized to operate suitable alarm and control circuitry. Photoelectric switches of this latter general type are well known in the art, as exemplified, for example, by U.S. Pat. No. 2,521,479.

Returning now to the system of FIG. 1, the conduit 74 also feeds a pressure regulator diagrammatically illustrated at 80. The pressure regulator senses the downstream pressure by way of sensing conduit 82 and may be set by means of adjustment 84 to a desired pressure level. The pressure regulator then serves to control the rate of flow of oxygen through conduit 86 which leads to inlet conduit 60 and thence to chamber 28 of cylinder 10. Interposed in conduit 86 is a metering valve 88 which is in effect a variable throttle that provides a fine degree of control over the flowrate of oxygen supplied to inlet conduit 60. The setting of metering valve 88 is adjusted by means of a suitable throttle linkage and control dial 90 or the like. An "add oxygen" switch 92 is connected to the throttle linkage to provide a control signal which is used, as will be described, to operate solenoid 70 when oxygen is to be added to the breathing gas. It will be noted that metering valve 88 limits the flowrate of the gas flowing in conduit 86 so that a controllable percentage of oxygen can be mixed with the air being drawn into the cylinder from conduit 54, for if the oxygen pressure at the junction of conduits 86 and 60 exceeds that of the atmosphere, only oxygen will be delivered to cylinder 10. Check valve 58 prevents the oxygen from venting to the atmosphere in such an event.

The motion of weight 24 within cylinder 10 is regulated by the pressure in upper chamber 26 which thus serves as a control chamber. This chamber is provided with a control passage 94 which is connected by way of a conduit 96 through a solenoid-controlled cylinder lift valve 98, having a solenoid 100, and thence by way of conduit 102 to a vacuum pump 104. Connected to conduit 102 is a variable pressure regulator 106 which is adjusted to admit a selected flow of atmospheric air into conduit 102, thereby regulating the vacuum drawn by pump 104.

When vacuum pump 104 is operating and lift solenoid 100 has been energized, a vacuum is drawn in control chamber 26 which may be adjusted by pressure regulator 106 to be of sufficient strength to lift weight 24. It will be apparent that the greater the vacuum in chamber 26 the faster weight 24 will be lifted, and therefore pressure regulator 106 serves to control the rate at which the weight is lifted. Deenergization of the lift solenoid 100 after weight 24 has been lifted will retain the vacuum in chamber 26, since the system is air tight, and accordingly the time at which the lift valve is deenergized will control the distance that the weight travels upwardly and thus will control the volume of the lower chamber 28. Control of the lift valve may be accomplished by comparing the output of the potentiometer with a preset level value so that when the two are equal, indicating that the desired height has been reached by the weight, the lift valve can be deenergized, as will be described below.

To release the weight 24 and to allow it to move downwardly in the cylinder on an air delivery stroke, the vacuum in chamber 26 must be released. This is accomplished by means of a cylinder lower valve 108 which, when energized by lower valve solenoid 110, admits air at atmospheric pressure from conduit 112 through conduit 114 and conduit 96 to the control passage 94. Interposed in conduit 114 is a metering valve 116 which is adjustable by means of a throttle linkage 118 to limit the rate at which atmospheric air will bleed into the control chamber.

The air delivery portion of the respirator may now be seen to operate as follows. Lift valve solenoid 100 is energized to connect the vacuum pump 104 to control chamber 26, raising weight 24 and expanding delivery chamber 28. The upward motion of the weight and of the diaphragm 18 draws air into the lower chamber by way of inlet 46. If extra oxygen is to be applied to the patient, the oxygen supply valve 66 is energized, and metering valve 88 adjusted to provide the required flow. The breathing gas is drawn into the chamber at substantially atmospheric pressure until the desired quantity has been drawn in, as determined by the location, or height, of the weight 24. The lift valve solenoid is then deenergized, closing valve 98 and holding the weight in a loaded, or charged, position until such time as air is to be supplied to a patient on the inspiratory mode of a breathing cycle. When the inhalation mode is initiated, the lowering valve solenoid 110 is energized to permit air to bleed into chamber 26 at a rate limited by the setting of metering valve 116. The air bleeding into control chamber 26 releases weight 24, allowing it to descend at a rate limited by the bleed rate, whereby the breathing gas in chamber 28 is discharged under pressure through outlet 50 and check valve 52 into an outlet conduit 120.

Weight 24 moves downwardly solely under the influence of its mass, restrained only by the rate of flow of air into the control passage 94 and the back pressure presented at outlet conduit 120 to the discharge chamber 28. The pressure produced in the discharged gas is limited, therefore, by the mass of weight 24, which in the preferred embodiment of the invention is approximately 26 lbs., and by the dimensions of chamber 10. Further, the volume of breathing gas that can be delivered by the air delivery cylinder is limited to the quantity drawn into chamber 28 prior to the downstroke or delivery stroke of the weight, which quantity was measured by potentiometer 40 (as a function of drive weight location) and directly indicated by mechanical indicator 38 prior to the start of the downstroke. Accordingly, only a predetermined quantity of breathing gas can be delivered at a predetermined and limited rate, under a predetermined and limited pressure.

The weight 24 travels nearly all the way to the bottom of cylinder 10 on a delivery stroke, thereby discharging substantially all of the breathing gas from chamber 28. When the weight reaches its bottom position, a bottom switch, to be described, enables a control circuit to accept a signal from potentiometer 40 to produce a control signal which reenergizes lift solenoid 100 to quickly raise the weight to the desired volume setting, where it remains for a period of time prior to the next downstroke. The quick return of the weight at the end of an inhalation mode insures that the cylinder will always be ready for delivery of air in the event of an unexpected patient demand, and in addition provides a period of time for the weight to stop moving before the next stroke, thereby improving volumetric accuracy.

The oxygen inlet pressure sensing switch 76 provides a further safety factor in that it senses the pressure on conduit 74 and sounds an alarm if it remains high at a time when no oxygen is to be delivered to the cylinder. Such a condition could endanger a patient, for then oxygen could be delivered to the patient even when cylinder 10 is not cycling. Accordingly, pressure switch 76 performs two functions. If, when oxygen is being delivered to the system, there is not 30 psi in conduit 74 at the end of the upstroke of weight 24, an alarm will be sounded, for failure to attain this pressure level will indicate that insufficient oxygen is flowing through metering valve 88. Secondly, the pressure switch 76 determines whether the pressure in conduit 74 drops below 30 psi between upstrokes of the weight. The oxygen supply valve 66 is controlled in such a way that it closes at the end of each upstroke, and remains closed until the succeeding upstroke begins so that oxygen can be delivered to the cylinder only during the upstroke of weight 24. The closure of valve 66 is indicated by a drop in the pressure on line 74; failure of this pressure to drop indicates that valve 66 is inoperative or leaking and results in an alarm condition just prior to the beginning of the following upstroke.

The gas that is discharged by the downward motion of weight 24 is delivered under pressure by way of conduit 120 and conduit 122, through an inspiration lock-out valve 124, conduit 126, bacteria filter 128, conduit 130, humidifier 132 and conduit 134 to the inspiration chamber 136 of a conventional patient breathing manifold 138. The air so delivered to the patient's lungs by way of a conventional inspiration conduit 140.

The inspiration lockout system functions by closing valve 124 at any time, within the hold and exhalation portion of the breathing cycle, during which an attempt, by the patient, to inhale results in a reduction of pressure to a level below ambient in conduit 126. During this hold and exhalation mode the lockout control valve 144 is energized, by means of solenoid 148, in order to allow an ambient pressure to be introduced into the pneumatic valve operator 146. While this condition exists, any pressure reduction below ambient in conduit 126 produces a differential pressure across the pneumatic valve operator 146 resulting in the shifting of valve 124 to a closed condition, effectively preventing any flow of gas through the valve.

During the inspiration portion of the breathing cycle, when it is desireable to have the patient receive air from cylinder 28, the lockout solenoid 148 is de-energized allowing the lockout control valve 144 to shift to a condition in which any pressure produced in conduit 126 will be conducted through conduit 142 and valve 144 to pneumatic valve operator 146. While this condition exists, no differential pressure can be produced across the pneumatic valve operator by a pressure variation in conduit 126, therefore valve 124 remains open to a flow of gas from cylinder 28 to the patient.

Since a failure of electrical power would also have the effect of de-energizing lockout solenoid 148, all of the conditions which exist for the lockout valve 124 during the inspiration mode would still be present. This would have the effect of allowing the patient to obtain breathing gas through cylinder 28 even though all of the powered functions of the respirator system were inoperative. Although a particular lock-out arrangement is illustrated, it will be understood that various other arrangements can be adapted into this system to provide the desired function.

The bacteria filter 128 and the humidifier 132 provided in the inspiration line leading to the breathing manifold may be conventional, commercially available items which are used to insure that clean, warm moist air is delivered to the patient. To provide a measure of the amount of oxygen actually being delivered to the patient, an oxygen monitor 150 may be connected to conduit 130 to obtain a sampling of the gas flow at that point. A suitable instrument for this purpose is model no. 300DPNB-10307C oxygen monitor produced by Teledyne Analytical Instruments Company. A meter is provided in combination with this monitor and is calibrated to provide an indication of the percentage of oxygen present in the breathing gas.

The patient breathing manifold 138 similarly is a commercially available item, and may, for example, be a Med Econ volume respirator manifold manufactured by Med Econ Plastics Inc., or its equivalent. This manifold incorporates a thermometer 152 for monitoring the temperature of the breathing gas at the inlet side of the manifold, and also incorporates a nebulizer 154.

The nebulizer 154 is operated by means of pressurized breathing gas supplied by a suitable air pump 156 having its inlet connected by way of conduit 158 to the outlet conduit 120. The outlet of the pump is connected by way of conduit 160 to a nebulizer control valve 162 which, when deenergized, recirculates the outlet gas in conduit 160 through return conduit 164 to the inlet of the pump. Since the nebulizer is only to be operated during the delivery of breathing gas to the patient, the operation of the nebulizer control valve 162 is synchronized with the cylinder lowering valve solenoid. Thus, the nebulizer valve solenoid 166 is energized during the lowering of cylinder 24 to deliver air from pump 156 through the valve to conduit 168, through a bacterial filter 170, and thence to the nebulizer 154.

During the exhale mode of the breathing cycle, the patient's lungs are connected by way of expiration conduit 172 through an expiration passage 174 to an expiration chamber 176 in the patient breathing manifold. The exhaled air then is discharged through an outlet passage 178 and is vented to atmosphere through a check valve 180. As long as the patient is capable of producing a positive exhalation pressure, the exhaled air can follow this path.

In order to prevent the patient from breathing in unfiltered and untreated atmospheric air from the expiration chamber of the manifold during an inhalation mode, an inflatable balloon valve 182 is provided at the end of passage 174, and is adapted when inflated to close off this passage to any flow of air toward the patient. The balloon valve is in the nature of an air-filled bag which may be expanded to close off passage 174 and contracted to open the passage. The operation of valve 182 is controlled by air pressure delivered through an expiration control valve 184 which is operated by an expiration solenoid 186. The control valve 184 connects the positive pressure side of vacuum pump 104 (FIG. 1) by way of conduits 188, 190 and 192 to the balloon valve. A pressure regulator 194 connected to line 188 produces a preset pressure level, whereby air from pump 104 expands valve 182 and closes passage 174 during the inspiration mode. This effectively prevents the patient from exhaling and insures that the breathing gas supplied to the manifold will be directed to the patient's lungs.

During the inflation hold portion of the breathing cycle, balloon 182 remains inflated and keeps passage 174 closed. During this mode, cylinder 10 is no longer delivering breathing gas, and the check valve 52 becomes operative also to prevent a flow of expiratory gases. Accordingly, the air delivered to the patient during the inspiratory mode is held in the patient's lungs until the start of the expiratory mode. When the patient is to exhale, the expiration solenoid 186 is energized to shift control valve 184 and vent conduit 192 to atmosphere by way of the lower valve connector, indicated by arrow 195 in valve 184, conduit 196, outlet passage 178 and check valve 180. This releases the pressure in balloon valve 182, allowing it to collapse and permitting the patient to exhale through passage 174, chamber 176, passage 178 and check valve 180 to the atmosphere.

When the patient exhales in the normal manner through check valve 180, he creates a positive exhalation pressure in chamber 176, and in chamber 136 as well, and forces the check valve 180 to open. However, in some circumstances, as where the patient is unable to exhale sufficiently well on his own, and to increase the patient's venous return, it may become necessary to produce a vacuum in chamber 176 to assist the patient to exhale and to produce a negative and expiratory pressure. This negative pressure is provided by a Neep Venturi 198 which is connected to the outlet passage 178 by way of conduits 200 and 196. Conduit 200 leads to the side wall of the Venturi tube through which a flow of air is produced, the Venturi effect operating in a manner to draw a vacuum in conduit 200 and thus in chamber 176. Because this vacuum is drawn during an exhalation mode and the expiration solenoid 186 is energized, the negative pressure generated by Venturi 198 is applied by way of conduits 196 and 192 to the balloon valve 182, collapsing the valve so that it cannot be extended by the vacuum in chamber 176 to close off passage 174.

The air flow through the Venturi tube 198 is provided by the positive pressure generated by vacuum pump 104, and is applied by way of conduit 188 through an exhalation assist valve 202, and thence through a conduit 204 to the Venturi 198. When it is desired to provide an expiration assist or a negative end expiratory pressure the Neep solenoid 206 is energized to shift valve 202, thereby producing a flow of air through the Neep Venturi which generates the negative pressure in chamber 176, as has been explained. Again, at the end of an expiration mode, Neep solenoid 206 is deenergized to permit the system to shift over to the inspiration mode.

Associated with the breathing manifold 138 are a plurality of sensors which respond to the pressure in the inspiration chamber 136 to provide various monitoring, override, and alarm signals. As illustrated in FIG. 2, these sensors are connected to the inspiration chamber 136 of the breathing manifold by way of a conduit 208, a humidity isolator 210, which functions to remove excess moisture from the air in conduit 208 to prevent damage to the pressure-sensitive switches and sensors, and conduit 212. A pressure gauge 214 is connected to conduit 212 to provide a visual readout of the pressure in chamber 136. An orifice, or metering valve, 216 is provided in conduit 212 to dampen the response time of the sensors and gauges to changes in the pressure within chamber 136.

Also connected to conduit 212 is a low pressure limit switch 218 which senses the pressure delivered to the patient and sounds an alarm if, at the end of the downstroke or inhalation mode, the pressure has not reached at least 8 cm. of water. Thus, when at the end of each downstroke the low pressure limit switch circuit is energized, or strobed, if the pressure limit switch is not closed to indicate that the desired pressure has been reached, an alarm is activated. This is a non-latching alarm, and is self-cancelling when the machine recycles in a non-alarm condition.

A sensitivity switch 220 is connected to conduit 212 and is adjustable to establish the pressure level which the patient must generate within the breathing manifold in order to override the automatic rate cycling control of the system. The sensitivity switch thus controls the demand assist mode of the machine, and permits a gradual change from the fully automatic mode of breathing to a demand breathing, thereby permitting the operator of the machine to gradually wean a patient, who has been under full automatic control, from dependency upon the respirator. Thus, the sensitivity adjustment permits the machine to be shifted between a full control mode where the breathing is fully automatic, and an assist mode, where the breathing rate is determined by the patient, and allows selection of any combination of these modes so that the needs of the patient can be met.

It will be apparent that the sensitivity control must have a minimum setting so that the machine won't become self-triggering; thus, there must be a definite effort by the patient, reflected as a negative pressure in chamber 136, before the sensitivity control will override the automatic cycle and initiate a new breathing cycle.

A normal pressure limit switch 222 is connected to conduit 212 to establish a maximum pressure in the breathing manifold during normal breathing cycles. This switch is adjusted to the desired limit, and if this pressure is reached for any reason during the delivery of air to the patient, the delivery mode is aborted, the drive weight 24 (FIG. 1) is immediately shifted from the downstroke to its upstroke operation, and an alarm is sounded. It will be noted that by means of switch 222 the present system may be operated as a pressure limited system rather than a volume limited system. This is accomplished by adjusting the stroke of cylinder 10 to produce an excess volume of air, and by adjusting the pressure limit switch 222 to the pressure level desired at the end of each inspiration. The pressure switch will then operate to shift the system out of the inspiratory mode before the weight 24 delivers its full volume of breathing gas. Although operating in this mode will cause an alarm to occur at each cycle, nevertheless this mode is available for those situations where it is desirable, thus increasing the flexibility of the present system.

A sigh pressure limit switch 224 is connected to conduit 212 and functions during a sigh breathing cycle. When operative, switch 224 functions in the manner of the normal pressure limit switch 222. As it is known in the respirator art, it is desirable periodically to introduce to the patient's lungs a greater volume of air than that of the normal breath cycle. This function, which is known as a sigh, is provided by the present system, and occurs at selected intervals. During a sigh cycle, the normal pressure limit switch 222 is disconnected from the control circuit, and the sigh pressure switch 224 replaces it.

The final sensor connected to conduit 212 is the Peen/Neep sensor switch 226 which is adjustable by means of control linkage 227 to control a selected level of positive or negative pressure occurring at the end of an expiratory mode. When the Peep/Neep sensor is positioned to produce a preselected level of positive end expiratory pressure (Peep) the sensor switch 226 enables the patient, during exhalation, to freely exhale to the atmosphere until the desired Peep level is reached. When the pressure during exhalation drops to the Peep level the sensor switch 226 deenergizes the expiration control solenoid 186 permitting the expiration of presurized air from the positive pressure side of the vacuum pump 104 (FIG. 1) to close the manifold balloon valve 182 thereby preventing the pressure from dropping significantly below the desired Peep level during exhalation. If the pressure, during the exhalation period, increases above the preselected Peep level the sensor switch 226 energizes the expiration control solenoid 186 permitting the expiration control valve 184 to shift causing the manifold balloon valve 182 pressure to drop enabling the patient to freely exhale to the atmosphere thereby permitting the pressure to drop to the desired Peep level again.

When the Peep/Neep sensor is positioned to produce a preselected level of negative end expiratory pressure (Neep) during the exhalation period, the sensor switch 226 regulates the patient's pressure at the desired Neep level. When the patient's pressure has been reduced to the desired Neep level the sensor switch 226 deenergizes the expiration control solenoid 186 permitting the expiration control valve 184 to provide pressurized air from the positive pressure side of the vacuum pump 104 (FIG. 1) to close the manifold balloon valve 182 thereby preventing the pressure from becoming more negative than the desired Neep level during exhalation. If the pressure, during the exhalation period, becomes less negative than the desired Neep level the sensor switch 226 energizes the expiration control solenoid 186 permitting the expiration control valve 184 to shift causing the manifold balloon valve 182 pressure to drop enabling more breathing gas to be withdrawn from the patient reducing the patient's pressure to the desired Neep level again.

The control system which is utilized to operate the pneumatic arrangement illustrated in FIGS. 1 and 2 is shown in functional form in FIGS. 4–7, with the circuit details being illustrated in FIGS. 9–17. The circuit components utilized in this control system are conventional, commercially available logic elements manufactured by numerous companies. For example, Texas Instruments Corporation of Dallas, Texas, Signetics Corporation of Sunnyvale, california, Stewart-Warner Company of Sunnyvale, California, and numerous other manufacturers provide the necessary components on an off-the-shelf basis. Essentially, the present system utilizes conventional series 7400 logic as follows:

| TYPE | DESCRIPTION |
| --- | --- |
| 7400 | Quadruple 2-Input Positive Nand |
| 7402 | Quadruple 2-Input Positive Nor |
| 7404 | Hex Inverters |
| 7410 | Triple 3-Input Positive Nand |
| 7420 | Dual 4-Input Positive Nand |
| 7440 | Dual 4-Input Positive Nand |
| 7474 | Dual D-Type Edge-Triggered Flip-Flop |
| 7475 | 4-Bit Bistable Latch |
| 7490 | Decade Counter |
| 74107 | Dual J-K Master-Slave Flip-Flop |
| 74121 | Monostable Multi Vibrators |
| 74153 | Dual 4-Line-To-1-Line Data Selector/ Multiplexer |

In addition to the foregoing logic elements, the system also utilizes type LM311 voltage comparators manufactured, for example, by National Semiconductor of Santa Clara California, type NE 555 timers, manufactured by Signetics of Sunnyvale, California, type CA3059 zero-voltage switches, manufactured by RCA Corporation, Somerville, New Jersey, type U2T301 Darlington Power Drivers from Utitrode Company of Watertown, MASS, and numerous other commercially available components. The photoelectric switches used in conjunction with the pressure sensing gauges, 76, 218, 220, 222, 224 and 226 may be a type 13B2, Photon Coupled Interruptor Module manufactured by General Electric Company of Syracuse, New York.

Since the functional diagram of FIGS. 4–7 corresponds to the schematic logic diagram of FIGS. 9–17, these two sets of drawings will be considered together, with corresponding elements, components or network being similarly numbered.

Figure 10:
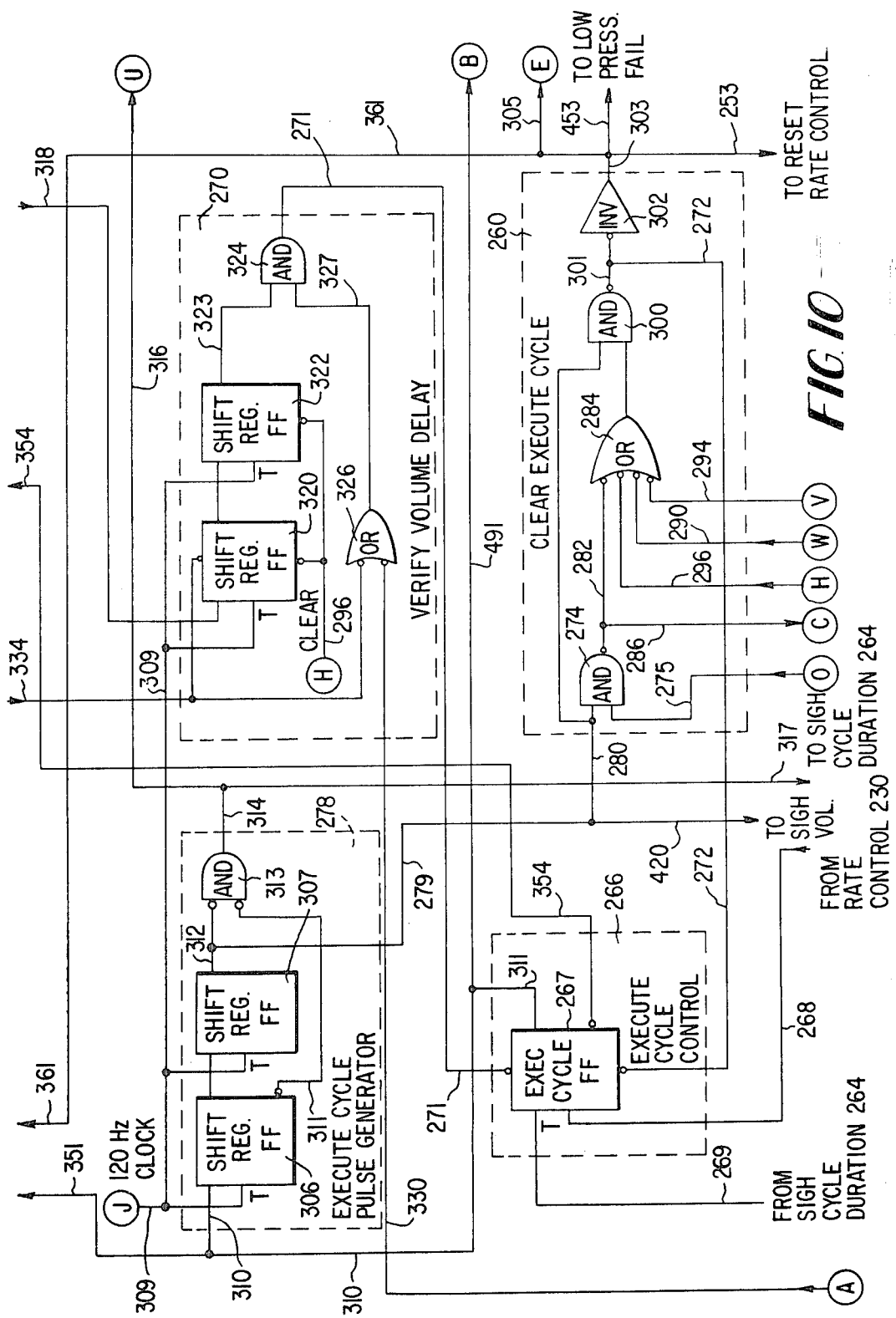
Figure 11:
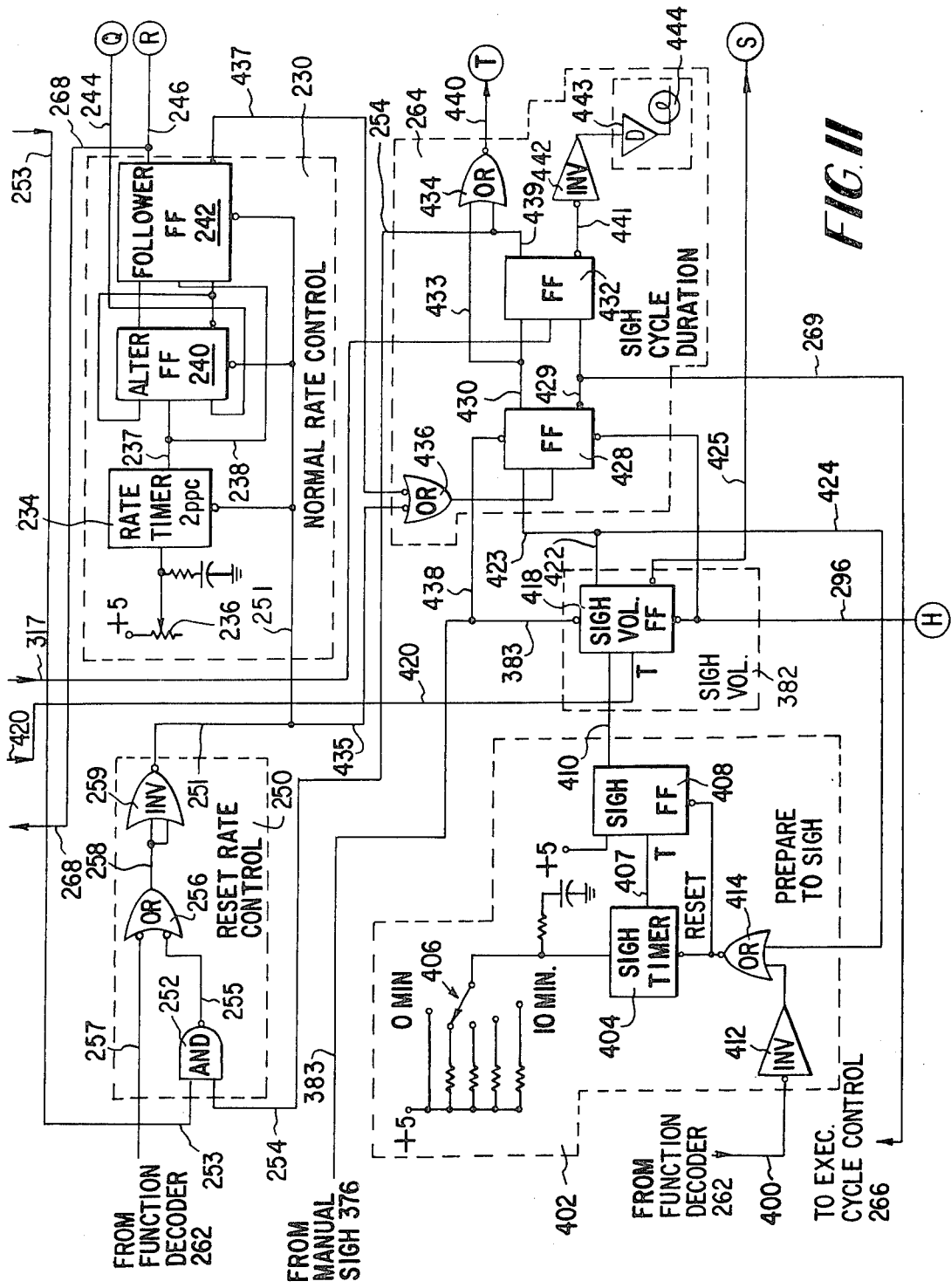

Reference will first be made to FIGS. 4, 5, 9, 10 and 11 which illustrate some of the basic control features of the invention, and which illustrate the normal rate control generator 230 which functions to produce the basic rate control signal for controlling the operation of the system. As seen in FIG. 11, the normal rate control circuit consists of a rate timer 234, which may be an astable multivibrator. The timer produces a train of pulses having repetition rate determined by a rate potentiometer 236 which preferably is located on the control panel of the respirator system. The rate potentiometer may be adjusted to cause the timer to produce a pulse having a repetition rate of between 0.5 and 25 seconds, with the timer producing two pulses for each breathing cycle τ of the respirator. (see timing diagram, FIG. 19). The timer output is fed by way of lines 237 and 238 to the timing inputs of a pair of phase register flip flops 240 and 242. The registers are of the master-slave type which means that their output does not change until the trailing edge of a timing pulse is received. Flip flop 240 is wired to operate as an alternate action register so that the end of the first timer period pulse on line 237 sets the flip flop and the end of the second timer period pulse resets it. The two timer periods constitute a single breathing cycle, with the end of the first timer period indicating the half way point in the cycle.

The flip flop 240 is set at the end of the first timer pulse to produce a high voltage on its output line 244. At the end of the second timer pulse, flip flop 240 is reset and a low voltage appears on line 244, as illustrated by the timing diagram FIG. 19. However, the resetting of flip flop 240 results in the setting of follower flip flop 242. Thus, a high voltage appears alternately on lines 244 and 246, which voltages are used in the system to clock the operation of the breathing cycles, the high voltage on line 244 signaling the half way point of a breathing cycle and the high voltage on line 246 signaling the beginning of the next breathing cycle.

The high voltage appearing on line 244 is used to clock the ratio-error detector 248 at each half-cycle point. The occurrence of a high voltage on line 246 signals the end of a complete normal period and is used for ratio error detection in the sigh mode, as will be explained below.

The normal rate control 230 operates under the control of timer 234 to produce a constant breathing rate in accordance with the setting of potentiometer 236. However, when a manual or assist cycle occurs to produce a breathing cycle which overrides the automatic cycling, the rate control circuit 230 receives a reset signal from the reset rate control network 250 by way of line 251 to interrupt the current cycle, and to continue with normal rate cycling after the override ends.

The reset rate control network 250 (FIGS. 5 and 11) produces an output signal which is used to reset, or hold frozen, the rate timer 234 and the phase registers 240 and 242 by way of a high voltage on line 251 which is applied to the "clear" inputs of circuit elements 234, 240 and 242. The reset rate control network consists of an AND gate 252 which, upon receipt of two low signals by way of input lines 253 and 254 produces an output on line 255 to one terminal of an OR gate 256. A second input is applied to OR gate 256 by way of line 257, with the output of the OR gate being applied by way of line 258 and inverter 259 to line 251. When appropriate signals appear on both lines 253 and 254, or when an appropriate signal appears on line 257, an output is produced on line 251 which clears the normal rate control network. The functions which occur to produce the required signals on lines 253, 254 and 257 will become apparent from what follows hereinbelow. However, it may preliminarily be seen from FIGS. 4 and 5 that the signal on line 253 is produced by a clear execute cycle network 260, the signal appearing on line 257 is produced by the output from a function decoder 262, and the signal on line 254 is produced by an output from a sigh duration network 264. These signals produce a reset of the normal rate congenerator 230 in the event of a power clear signal (see FIG. 19), which occurs when the system is initially turned on, a manual breath, a manual sigh, the testing of the system in a test mode, the occurrence of a patient-triggered assist, or a clearing pulse in combination with the system being in the sigh mode.

The one element of the control circuit which affects almost every aspect of the controlling of machine operation is the execute cycle control network 266 (FIGS. 4 and 19). This network includes only one component, an execute cycle flipflop 267. The time during which this flipflop is set is the time of air delivery in the breathing cycle while the duration of reset is the time for preparing for the next actuation of the air delivery cylinder. The time at which the flipflop 267 is set and the time at which it is reset is used for starting and stopping various functions in the system (see FIG. 19)

The flipflop 267 is clocked; i.e., driven by a signal applied to its clock input T, to the set condition by the occurrence of a high signal on line 246 of the rate control network 230, which signal occurs at the start of the second half of the breathing cycle, and is applied to the clock input T of flip flop 267 through lines 246 and 268. Flipflop 267 is prevented from being set by this signal, however, if the sigh cycle duration network 264 is producing an output signal on line 269, which indicates that the system is in a sigh cycle and that the next breath should not occur in the regular time sequence. It should be noted that the duration of sigh varies according to the duration of the period of breath delivery and the breathing rate set by the operator. A sigh cycle is equal to the time of breath delivery (inhalation mode), as determined by the execute cycle flip flop 267, plus a full breath cycle, up to a duration of two breathing cycles at the set rate. A longer sigh cycle results in a sigh ratio-error. The variable length of time for the sigh cycle is created to prevent axiety on the part of a conscious patient who, for example, may have a fast breath delivery. If a fixed long sigh duration is provided, the contrast between the sigh and the normal breath rate could worry the patient; however, adjusting the length of sigh to correspond to a single cycle at the set normal rate plus a breath delivery period prevents this problem.

Flip flop 267 in the execute cycle control network 266 is directly set, without waiting for a pulse from the rate control network, in response to a manual breath or a patient-initiated breathing assist instruction. This direct set is provided by way of the function decoder 262, a verify volume delay network 270, and its output line 271, as will be explained. The flip flop 267 is cleared, or reset, by an output from the clear execute cycle network 260 by way of line 272.

Figure 7:
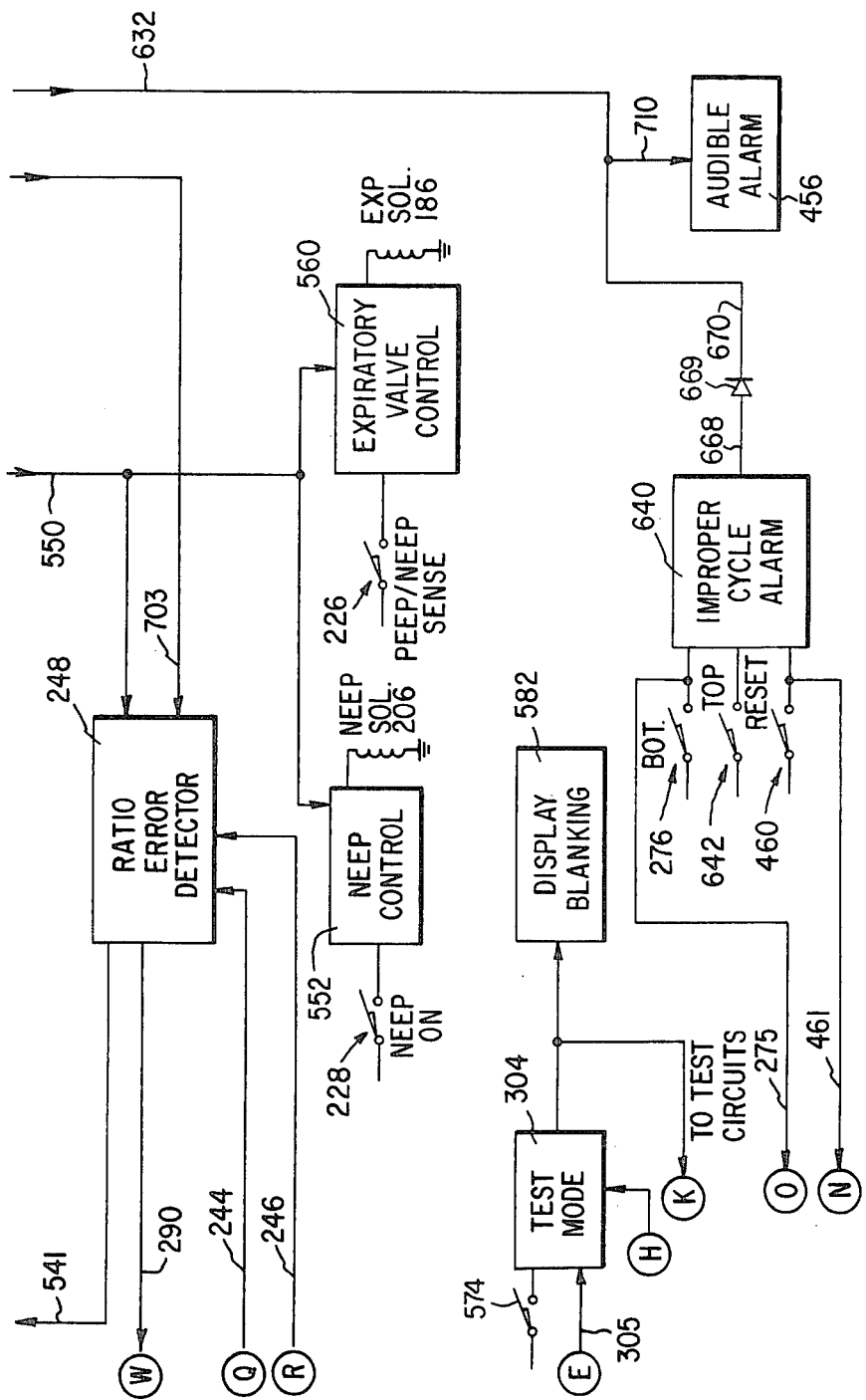
Figure 9:
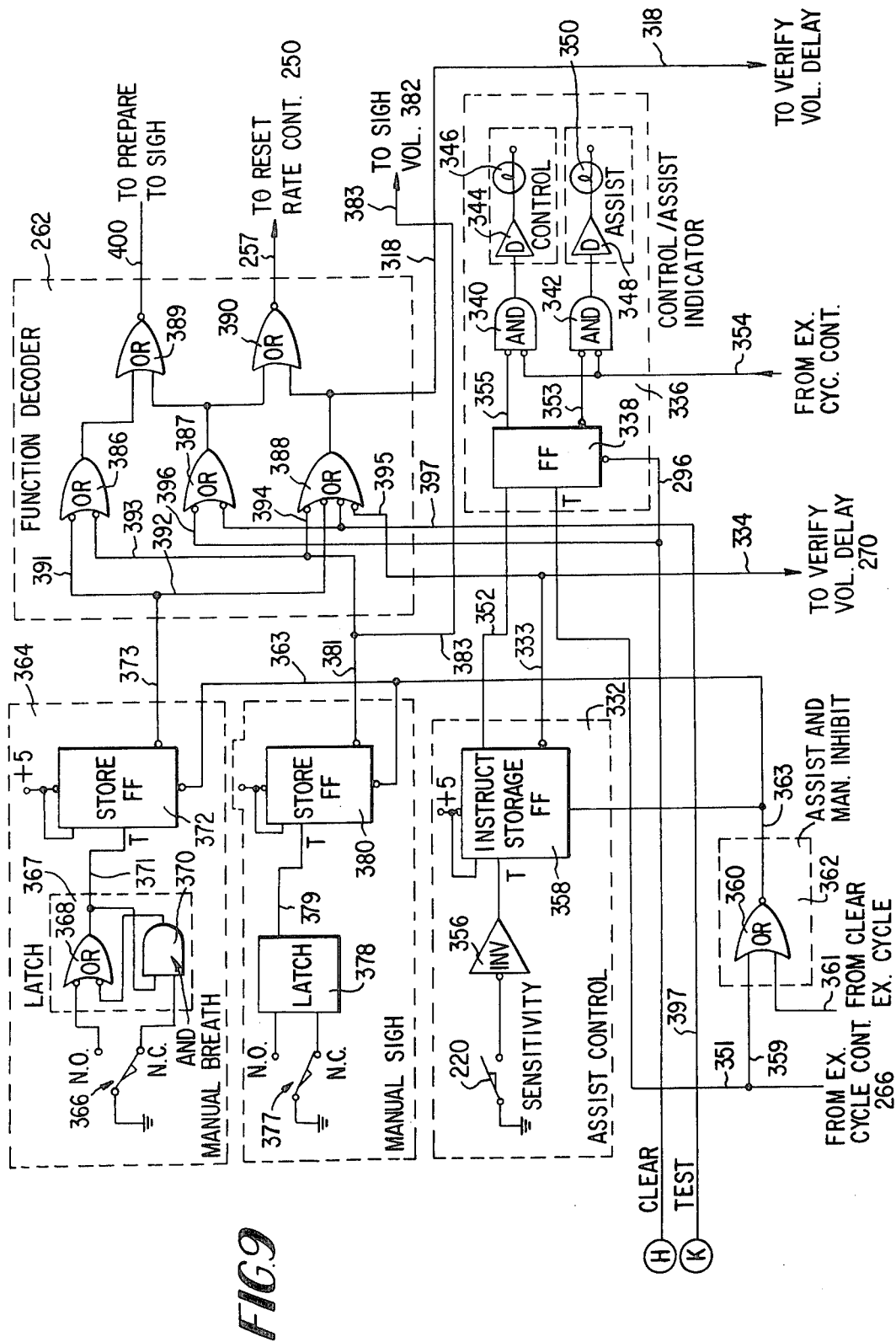
FIGS. 9 through 17 provide block diagram of the logic circuitry used in the respirator system of the present invention, corresponding to the functional diagram of FIGS. 4–7.
Figure 16:
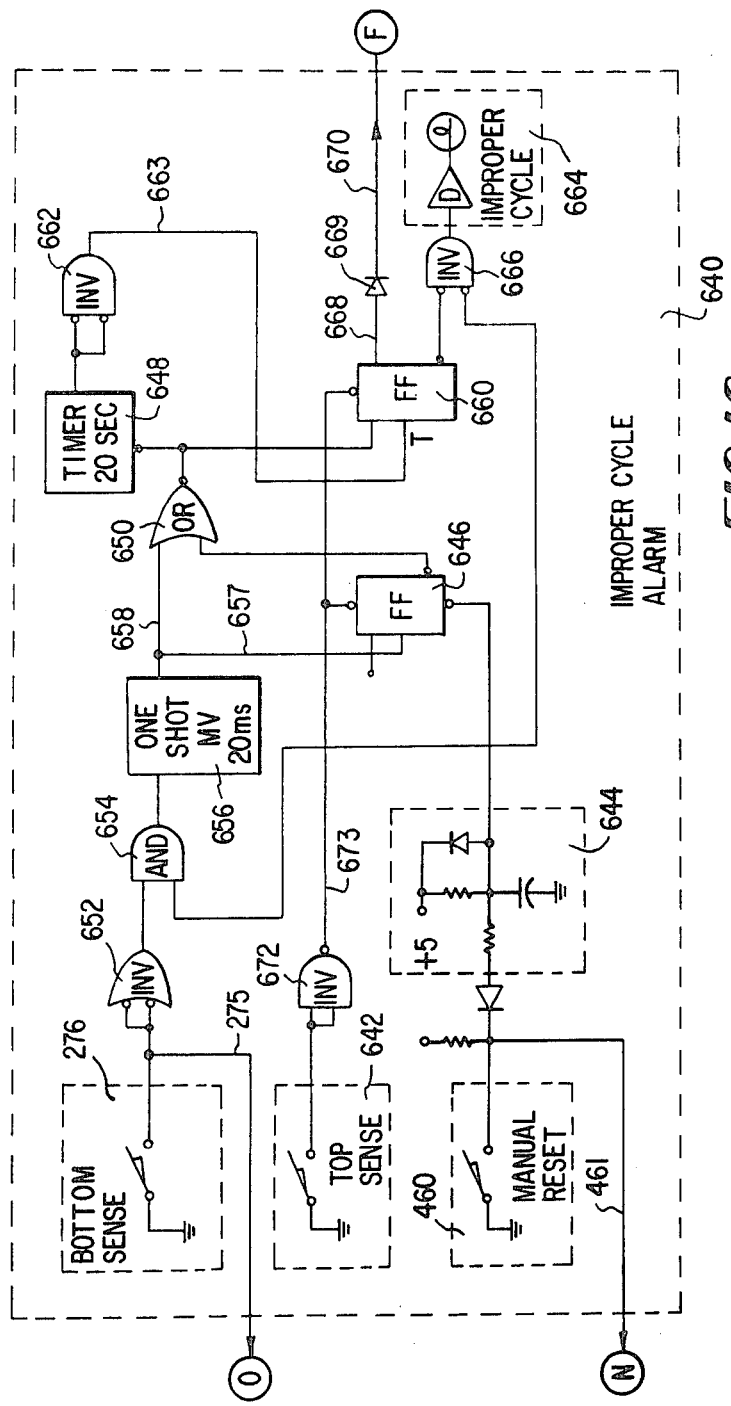

The clear execute cycle control network 260 is a gate that provides the command to clear the execute cycle flip flop 267. This network consists of a series of gates which produce a clearing signal on line 272 upon the occurrence of selected system functions. This network includes an AND gate 274 which receives an input signal on line 275 when the air delivery cylinder drive weight 25 bottoms out, as determined by bottom switch 276 (FIGS. 7 and 16). The connection between switch 276 and gate 274 is not shown in its entirety, for purposes of clarity, but the terminal indicator (the letter O in this case) indicates a common connection. This labeling system is used in order to eliminate the need for including all of the multitude of connecting lines that would be required in this system to connect all of the various points. Thus, points labeled with corresponding letters are interconnected in the actual circuitry of the system.

The second input to AND gate 274 is a delayed output pulse from an execute cycle pulse generator network 278 by way of lines 279 and 280. The output from AND gate 274 is applied by way of line 282 to one of the inputs of an OR gate 284 within the clear execute cycle network 260. The voltage on line 282 is also applied by way of line 286 (terminal c) to an inflation hold control network 288 (FIGS. 6 and 14), this signal acting as a start hold signal to initiate the inflation hold time. Thus, the start of the inflation hold mode, or phase, of the cycle occurs when the cylinder drive weight reaches the bottom of the cylinder, at the end of the air delivery phase (inhalation mode).

Figure 6:
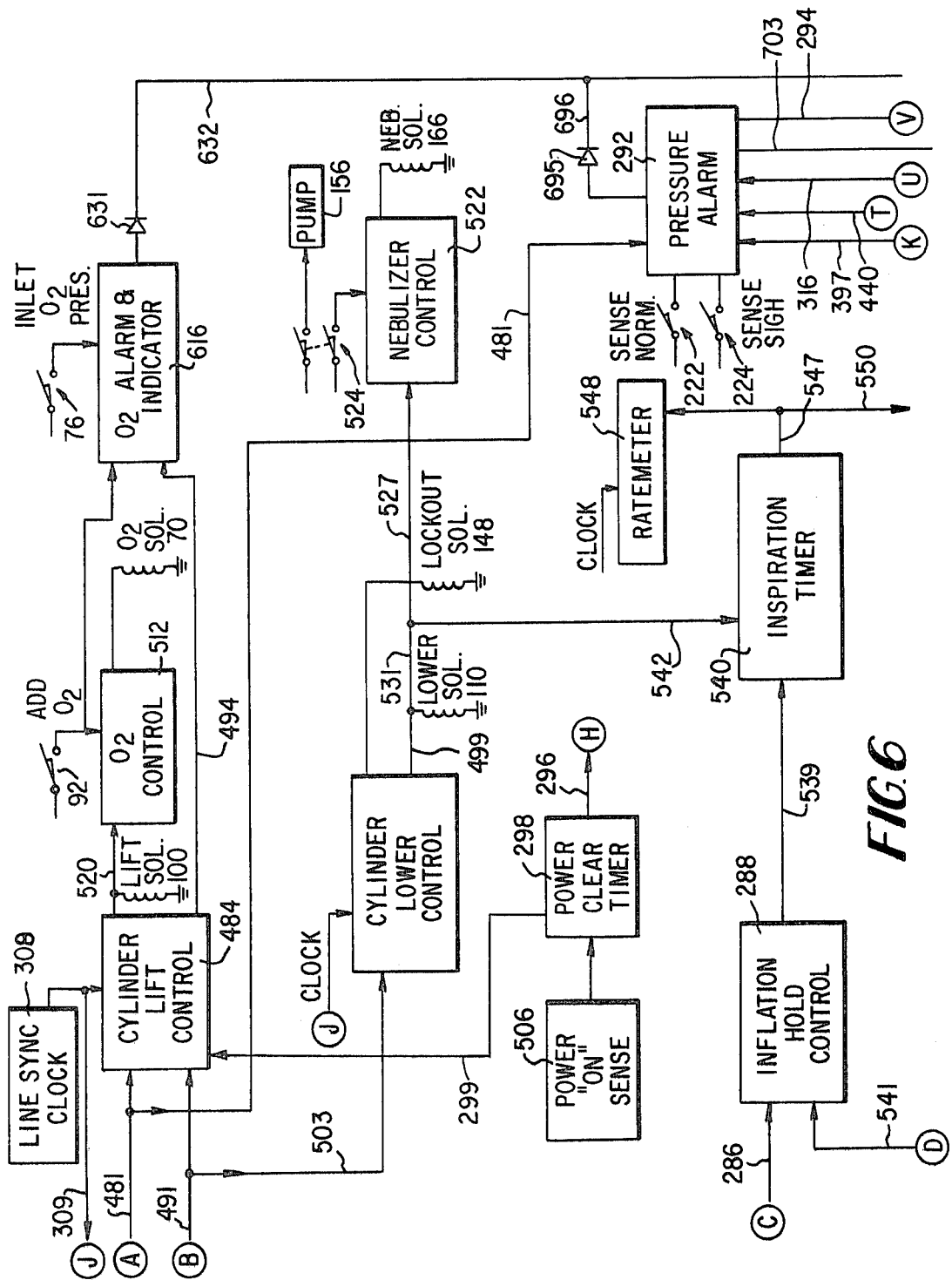

Three other signals are used to provide clearing pulses to the OR gate 284. The output from the ratio-error detector network 248 is applied by way of line 290, the output from a pressure alarm network 292 by way of line 294, and a power on clear signal on line 296 produced by a power clear timer 298 (FIG. 6). An output from gate 284 is applied to AND gate 300 in network 260 together with the delayed output from the execute cycle pulse generator 278 appearing on line 280. When these signals are gated, a pulse is produced on lines 301 which is carried by line 272 to clear the execute cycle control flip flop 267. Because the delay pulse on line 280 is controlled by the system clock, it has a minimum duration of 8.3ms; therefore the signal on line 272 has the same duration to insure that flipflop 267 is cleared. The output of AND gate 300 is also applied by way of line 301 to an inverter 302, thereby producing a clear execute cycle signal on output line 303 for application to additional control networks to be described. One of the networks to which the output on line 303 is applied is the test mode control network 304, the output being delivered from inverter 302 to clear the test mode control network.

The execute cycle pulse generator network 278 is used to generate an 8.3ms pulse at the beginning of the execute cycle time. The network also provides a delayed pulse which occurs a minimum of 8.3ms or a maximum of 16.7ms after the beginning of the execute cycle time, producing an execute cycle pulse having that same duration. The execute cycle pulse generator 278 comprises a two-bit shift register made up of a pair of flipflops 306 and 307, both of which are driven by the 120 Hz pulses from the system clock generator 308 (FIG. 13) by way of line 309 (terminal J), which signals are applied to the timing inputs of the two flipflops.

The input to the execute cycle pulse generator is provided by way of line 310 leading from the output 311 of the execute cycle flipflop 267, which line has a high signal when flipflop 267 is set. When a high signal is applied to shift register flipflop 306, the leading edge of the next clock pulse that is applied to the timing input will set flipflop 306, producing a low signal on output line 311. Since this first timing pulse will not set shift register 307, its output line 312 remains low so that both inputs to AND gate 313 are enabled. This produces a high signal on output line 314 from the execute cycle pulse generator. One clock pulse later, the flipflop 307 will be set, line 312 will go high, and the output of AND gate 313 will drop. The shifting of AND gate 313 produces a pulse lasting 8.3ms at the beginning of the execute cycle time, which pulse is initiated by the appearance of a signal on execute cycle control network output line 311. The output pulse appearing on line 314 is directed by way of line 316 to connector point U, and thence to the pressure alarm network 292. This pulse is also applied by way of line 317 to sigh cycle duration network 264. The shift register in network 278 can only be cleared by the removal of the input execute cycle signal on line 310, followed by two 120 Hz clock pulses.

Thus, the output on line 312 is the execute cycle time, delayed by 8.3ms, to 16.7ms.

The verify volume delay network 270 prevents the start of a manual normal or manual sigh breathing cycle until a check is made to insure that an adequate volume of air is present in the cylinder delivery chamber. Thus, an instruction from the manual breath control will be delayed until the cylinder is at the set volume; thereafter, the breathing cycle can be initiated. When the system is in the breathing assist mode, and thus is under the control of the patient, it is desirable that the system respond immediately to the patient's demands, and accordingly an assist control signal produced by the sensitivity control switch 220 will defeat the volume verify and delay network.

A manual or assist control instruction is fed to the network 270 by way of function decoder 262 and line 318. This signal is applied to the input of a first shift register flip flop 320 in delay network 270. This network also includes a second flip flop 322, with the two flip flops being set up as a two-bit shift register that is clocked by the 120 Hz clock pulse train on line 309. The flip flops are interconnected so that the presence of two successive clock pulses is required after receipt of the instruction signal on line 318 to drive the output line 323 of flip flop 322 high. This requirement provides a minimum delay of 8.3ms and a maximum delay of 16.7ms between the time the instruction is received and the production of a high signal on line 323. This delayed instruction signal is fed to an AND gate 324 where it is combined with the output from an OR gate 326 by way of line 327. OR gate 326 has two inputs; one input is received from a cylinder volume control network 328 which produces on its output line 329 an "at volume" signal when the cylinder has reached its predetermined volume setting. The "at volume" signal is applied by way of line 330 to the OR gate 326 and when this signal is present the two inputs to AND gate 324 are enabled to produce the verify volume signal on line 271. However, the AND gate 324 prevents the verify volume signal from being applied to line 271 until at least 8.3ms after the occurrence of a manual instruction; thereafter, the signal is available to produce a command input to the execute cycle control network 266. If the instruction being applied to the delay network 270 is an assist control signal supplied from an assist control network 332, the signal is fed by way of lines 333 and 334 to the OR gate 326 in delay network 270, as well as to the direct set terminal of flip flop 320. By direct setting the shift register, the delay between the receipt of an assist signal and the production of an output signal on line 271 is reduced by 8.3ms, which is the time between successive clock pulses, thus the shift register flip flop 322 will produce a high output on line 323 at the first clock pulse received after the assist instruction is present. The presence of the assist signal from line 334 at the OR gate 326 bypasses the requirement for an at volume signal on line 330, whereby the AND gate 324 also is enabled upon the occurrence of the first clock pulse to produce a command on line 271 which is fed to the execute cycle network. Thus, the requirement for an assist by the patient overrides the verify volume delay, and produces an execute instruction as soon as the next synchronizing clock pulse is received. The shift register flip flops 320 and 322 may be cleared by a power on clear signal on line 296 (terminal H) or by the disappearance of a manual or assist instruction.

A control/assist indicator network 336 (FIGS. 4 and 9) is provided to indicate to the operator of the respirator system whether the breath being delivered as a result of an execute cycle control signal was triggered by the machine under automatic control, or by the patient as a result of an assist demand. This indicator network consists of a flip flop 338 having its set and reset outputs connected to AND gates 340 and 342, respectively.

The output of AND gate 340 is connected through a driver amplifier 344 to a control indicator lamp 346, and the output of AND gate 342 is connected through a driver amplifier 348 to an assist indicator lamp 350, whereby enabling of one or the other gates will result in illumination of a corresponding indicator lamp. Flip flop 338 is driven by the pulse appearing on output line 311 of the execute cycle control network 266, which signal appears at the start of the breath delivery portion of the breathing cycle. This signal is applied by way of lines 311, 310, and 351 to the clock input terminal of flip flop 338. Whether the flip flop is set or reset by the pulse is dependent upon the presence or absence of an assist instruction from assist network 332 by way of line 352. If an assist signal is present, flip flop 338 will be set, producing a low output on line 353 to enable AND gate 342. In the presence of a low signal from the second output of the execute cycle control network 266, which signal appears on line 354, AND gate 342 is enabled, and the assist indicator lamp 350 will be turned on. If the assist instruction is not present on line 352, flip flop 338 will not be set, thereby producing a low output on line 355 to enable AND gate 340 and illuminate control lamp 346. Flip flop 338 is reset by the occurrence of a non-assist breath which produces a pulse on line 351 in the absence of an assist signal on line 352. The flip flop is also reset by a power clear signal on line 296 (terminal H).

As has been indicated, the assist control network 332 allows the patient himself to initiate a machine cycle. The breath which the patient initiates will be either a normal or a sigh breath depending on the state of the sigh control. If the assist occurs when a sigh is scheduled to take place, then the patient will initiate the sigh. The ease with which a patient can trigger the machine is determined by the setting on the control panel of the sensitivity pressure switch 220 (FIG. 2). When the vacuum produced by the patient's attempt to inhale operates the switch, the assist control network 332 (FIG. 9) is activated. The signal produced by the closure of switch 220 is inverted by inverter 356 and is applied to an instruction storage flip flop 358 which stores the instruction. Flip flop 358 can only be clock set by a signal applied to its clock input T by means of a pulse supplied by the inverter 356 so that only one assist breath can be produced for each new actuation of the sensitivity control. Flip flop 358 is responsive to the pulse from inverter 356 to shift to the set condition to produce a high signal on line 352 and a low signal line 333, which signals are supplied to the control/assist indicator 336 and to the verify volume delay network 270, as has been explained.

The flip flop 358 can only be directly cleared by an execute cycle pulse applied from network 266 by way of lines 311, 310, and 359 to an OR gate 360 in the assist and manual inhibit network 362, or by means of a clear execute cycle pulse from network 260 which is fed by way of lines 303 and 361 to the OR gate 360. When either of these signals is present at gate 360, an output is produced on line 363 which is applied to the clearing terminal of the flip flop 358. Thus, a signal from the execute cycle control network or from the clear execute cycle network will hold the flip flop 358 in its cleared condition to prevent the system from calling for an assist while a breath is already being delivered and, in addition, will clear the assist control after machine action has been initiated in response to the assist instruction.

A manual breath control network 364 is provided to prepare the machine for a manual breath operation. The control consists of a panel switch 366 having normally open (N.O.) and normally closed (N.C.) contacts. These contacts are connected to a bounce elimination latch 367 which is activated upon shifting of the switch contact 366 to produce a single output clock pulse in response to operation of the switch. The latch consists of an OR gate 368 and an AND gate 370 interconnected to produce the single output pulse even if the contacts should open and close, or bounce, several times. The output from latch 367 is applied by way of line 371 to the clock input of a storage flip flop 372, which stores the manual breath instruction. Flip flop 372 can only be clock set by the pulse on line 371, so that only one manual breath can be produced for each separate depression of the control switch 366. The setting of flip flop 372 produces a low signal on output line 373, which signal is supplied to the function decoder 362. Flip flop 372 is direct cleared by the clear execute cycle and execute cycle signals applied to OR gate 360 by way of lines 361 and 359, respectively, the output from the OR gate being applied to the clearing terminal of flip flop 372. Again, this prevents the system from calling for a manual breath while a breath is already being delivered, and also clears the instruction once the machine action has been initiated.

To permit the introduction of a manual sigh, the system includes a manual sigh control network 376 which is used to prepare the machine for performing a manual sigh operation. The control consists of a manual sigh control switch 377 which preferably is located on the control panel of the machine. The switch is connected through normally open and normally closed contacts to a switch bounce elimination latch 378, the output of which is applied by way of line 379 to the clock input of a storage flip flop 380, which stores the instruction. This flip flop can only be clock set by the latch output on line 379 so that only one manual sigh can be produced for each separate depression of the control switch. When the flip flop is set by a signal on line 379, a low output is produced on output line 381 for application to the function decoder 262 and to a sigh volume control network 382 (FIG. 11) by way of line 383. Flip flop 380 is direct cleared by the output from OR gate 360 in the assist and manual inhibit network 362 to prevent the system from calling for a manual sigh while a breath is already being delivered.

It will be apparent from what has been said that the assist and manual inhibit network 362 functions to gate the execute cycle and the clear execute cycle pulses on lines 359 and 361 to clear the storage registers of the manual normal breath network 364, the manual sigh network 376 and the assist control network 332 to prevent the system from calling for one of these functions while the machine is already delivering a breath. Further, this signal clears the manual or assist instruction from the respective storage flip flops after the machine has initiated the selected operation, as indicated by the existance of an execute cycle control signal, thereby clearing these flip flops after the instruction has been carried out.

Function decoder 262 receives the outputs from the manual, sigh, and assist control networks 364, 376 and 332 and produces specific command outputs for machine operation. The decoder consists of a plurality of OR gates 386 through 390. The output from manual breath network 364 is applied by way of lines 373, 391 and 392 to the inputs of OR gates 386 and 388. The output from manual sigh network 376 is applied by way of line 381 and lines 393 and 394 to OR gates 386 and 388, respectively. The output from network 332 is applied by way of line 333 and 395 to OR gate 388. In addition, the power on clear signal (to be described) from line 296 (terminal H) is applied by way of line 396 to OR gate 387 and a test signal from the test mode network 304 (FIGS. 7 and 14) is applied by way of line 397 (terminal K) to OR gates 388 and 387. The output of OR gate 386 is applied to gate 389, the output of OR gate 388 is applied to one input of OR gate 390, and the output of OR gate 387 is applied to both the OR gates 389 and 390. The function decoder provides three outputs, one output appearing on line 400 when OR gate 389 is enabled, one output appearing on line 257 when OR gate 390 is enabled, and one output appearing on line 318 when OR gate 388 is enabled.

The function decoder output line 257 is connected to OR gate 256 of the reset rate control network 250, whereby the normal rate control network 230 will have its operation reset by the occurrence of a power clear signal, a test signal, a manual sigh, an assist, or a manual normal breath, all of which produce corresponding inputs to the function decoder. This reset command thus produces an output on line 251 which resets the normal rate control network 230, as has been explained.

The output 400 from function decoder 262 is applied to a "prepare to sigh" control network 402 (FIG. 11) whereby network 402 will have its operation reset by the occurrence of a power clear signal, a test signal, a manual normal signal or a manual sigh. Finally, the function decoder is used to initiate the verify volume delay network 270 by way of line 318 to produce a volume delay prior to executing the power clear, test, manual normal or manual sigh operations.

The prepare to sigh control network 402 is used to inject sigh breaths into the machine operation at intervals chosen by the operator (see FIG. 19). This network includes a sigh timer 404 which is an astable, or free running, multivibrator having a variable time period that may be set by a selector switch 406 which preferably is on the control panel of the machine. The time set by the selector switch establishes the interval between succeeding sighs when a sigh operation is to be included in the machine. The timer 404 times out at the desired sigh intervals to produce a pulse on line 407 which is applied to the clock input of a sigh flip flop 408. This signal will clock set the flip flop at the sigh intervals to produce a high signal on output line 410 to indicate that the next automatic or assist breath will be a sigh.

An output signal from function decoder 262 is applied by way of line 400 to reset network 402 upon the occurrence of a manual breath, manual sigh, power on clear, or test instruction. The signal on line 400 is fed through an inverter 412 to an OR gate 414, the output of which resets the sigh timer 404 and the sigh flip flop 408. The resetting of the sigh timer upon the occurrence of a manual sigh instruction insures than an automatic sigh will not be produced by the time immediately after a manual sigh has been selected; the resetting of the timer insures that the next occurring automatic sigh will follow by the full selected interval.

Although an output signal on line 410 indicates that the system is ready for a sigh, the actual sigh control is provided by the sigh volume control network 382 which comprises a sigh volume flip flop 418 settable by the signal appearing on line 410. The sigh volume flip flop is driven by a pulse from the execute cycle generator 278, by way of line 279 and line 420, this pulse being applied to the clock input (T) of flip flop 418. When the prepare to sigh flip flop 408 produces a high signal on line 410, the next occurring pulse from the pulse generator 278 will set the sigh line flip flop 418, producing a high signal on output line 422 (see FIG. 19), which signal is fed by way of line 423 to the sigh cycle duration network 264. The output signal on line 422 is also applied by way of line 424 to OR gate 414 in the prepare to sigh network to reset the sigh timer and restart the sigh interval. When the flip flop 418 is set to initiate a sigh cycle, it provides a sigh volume low signal on output line 425 (terminal S) for use by the cylinder volume control 328.

If it is desired to bypass the automatic sigh interval so that the operator can produce a sigh operation manually, this may be accomplished by closing manual sigh contact 377 to produce a manual sigh output on lines 381 and 383 for application to the direct set input terminal of the sigh volume flip flop 418. This signal immediately sets the flip flop 418, producing the sigh instruction on line 422. The next following pulse from the pulse generator 278 will clock down the flip flop 418, removing the sigh instruction signal from line 422 and preparing the system for the next normal breath. Flip flop 418 is direct cleared only at the power on clear time by the power on pulse from line 296.

The sigh instruct signal 422 is applied to a flip flop 428 in the sigh cycle duration network 264, which network is used to provide signals for controlling the initiation and duration of a sigh cycle. The resultant low signal appearing on output line 429 of the set flip flop 428 is applied by way of line 269 to the execute cycle flip flop 267. This low signal adjusts the length of the sigh mode, to allow a sigh to last longer than a normal breath, by preventing the occurrence of an execute cycle command when the first time out of the rate period takes place during a sigh. Thus, the low input to flip flop 267 prevents the rate control network from setting that flip flop.

The setting of flip flop 428 also produces a high signal on its output line 430 to enable a second flip flop 432 and to provide an input by way of line 433 to an OR gate 434. The clock input of flip flop 428 is driven either by the reset rate control output from line 251 by way of line 435 and OR gate 436, or by the output signal appearing on line 437 from the normal rate control network 230. When it is driven by the output from OR gate 436, flip flop 428 will be set if the sigh volume flip flop 418 has been set.

It will be noted that a manual sigh instruction received on line 383 will direct set flip flop 428, by way of line 438, at the same time that flip flop 418 is direct set. Flip flop 428 is reset by the next succeeding pulse from OR gate 436, and thus is reset by either the output signal from the normal rate control network 230 or by one of the functions that resets the normal rate control, as determined by the function decoder 262 and reset control 250. Flip flop 428 is also direct cleared by the power on clear signal on line 296.

Flip flop 432 is a master-slave type that will be set at the end of the execute cycle pulse on line 317 which next follows the setting of flip flop 428. The setting of flip flop 428 to produce a high signal on line 430 is the start of the sigh delivery stroke, and this signal is applied by way of gate 434 to output line 440. The subsequent setting of flip flop 432 produces a high signal on output line 439 which is applied to the OR gate 434 in place of the high signal previously applied by flip flop 428, to produce a continuing sigh signal low output on 440 (terminal T). This signal tells the respirator system when a sigh cycle is occurring.

When flip flop 432 is set, a low output appears on line 441, and is inverted by inverter 442 to activate a sigh lamp driver 443 and its corresponding indicator lamp 444. Flip flop 432 remains set until the end of the execute cycle pulse on line 317. This occurs at the start of the next following breath, unless the following breath is another sigh, and the flip flop is clocked down, or reset.

Figure 12:
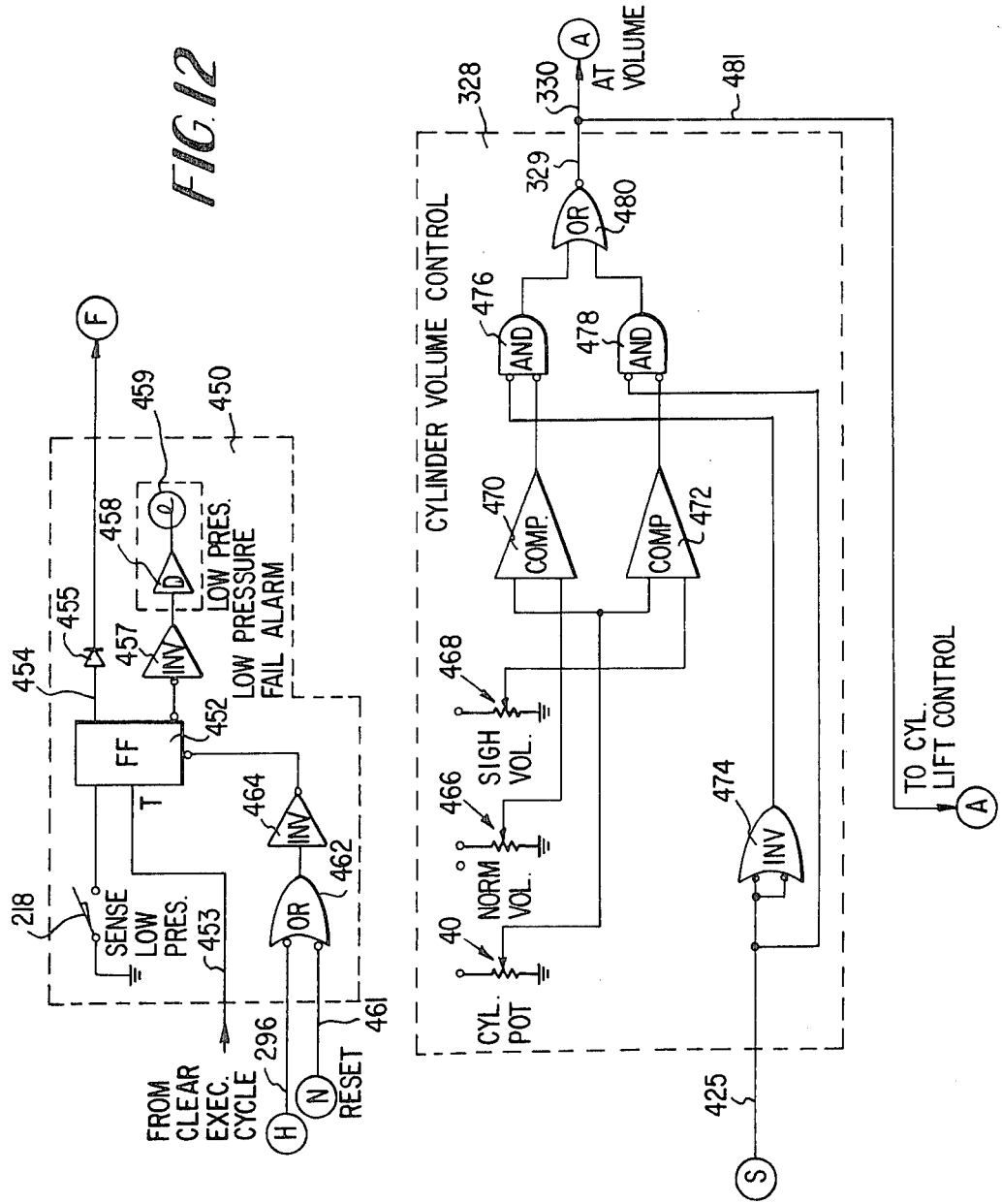

Turning now to FIG. 12, there is illustrated a low pressure alarm network 450 which is used to verify that by the end of the cylinder delivery stroke, the pressure at the patient manifold has reached at least 8cm of water. This alarm is used to check for a patient disconnect or any large leak. The alarm network includes a flip flop 452 which is driven by the clear execute cycle pulse which occurs at the end of the cylinder delivery stroke. This signal appears on line 303 (FIG. 10) and is applied to alarm network 450 by way of line 453. If 8cm. of pressure has been reached, the low limit pressure switch 218 will be actuated to provide a low input to flip flop 452 so that flip flop will remain reset. However, if the switch has not been actuated, its output will be high and the flip flop will become set upon the occurrence of a clear execute cycle pulse, producing a high output on line 454.

This high voltage on line 454 is applied by way of diode 455 to an audible alarm circuit 456 (FIGS. 7 and 17) by way of terminal F. When flip flop 452 is set, its low output is applied by way of inverter 457 to a low pressure lamp driver 458 and indicator lamp 459 to provide a visual alarm. The alarm is reset when the end of the next cylinder delivery stroke results in a pressure of at least 8cm, thereby opening switch 218. In addition, the alarm may be reset by the power on clear signal on line 296 or by the reset signal produced by a manual reset switch 460 (FIG. 16) by way of line 461 (terminal N). Both the power on clear and reset signals are applied through an OR gate 462 and an inverter 464 to the reset terminal of flip flop 452.

Also illustrated in FIG. 12 is the cylinder volume control network 328 which operates to compare the volume position of the cylinder with the normal breath and sigh volume settings on the respirator control panel. The measured cylinder volume is compared with the selected volume settings through the use of three potentiometers, the cylinder position potentiometer 40 (FIG. 1), a normal volume setting potentiometer 466, and a sigh volume setting potentiometer 468. The angle of rotation of the cylinder potentiometer corresponds to the volume in the delivery chamber 28, and the normal and sigh volume potentiometers 466 and 468 are similarly calibrated. Thus, for a given cylinder volume, the voltage from the wiper of the cylinder potentiometer will be equal to the wiper voltage of the control panel potentiometer which is set at that same volume.

A comparator 470 compares the voltage readings of the cylinder position potentiometer 40 and the normal volume potentiometer 466 to produce an error signal when the cylinder volume is differs from the volume selected by the normal volume setting. Similarly, the cylinder potentiometer voltage is compared with the sigh volume potentiometer voltage in a second comparator 472 which produces an output when these voltages are different.

The sigh volume signal on line 425 (terminal S) which is low when a sigh volume is to be delivered, is applied to the volume control network 328 through an inverter 474. The output of the inverter 474 is applied to an AND gate 476, while the low signal on line 425 is applied directly to a second AND gate 478. The output of comparator 470 is applied to AND gate 476, while the output of comparator 472 is applied to AND gate 478. When a sigh volume is selected by the presence of a low signal on line 425, AND gate 478 is enabled to permit the output of sigh comparator 472 to be gated through an OR gate 480 to produce a signal on lines 329 and 330 (terminal A) to be applied to the cylinder lift control by way of line 481. If the cylinder has reached the selected sigh volume, the output of comparator 472 will be low, the output of AND gate 478 will be high, and the output of OR gate 480 will be low, the resultant low signal on line 481 thereby indicating that the cylinder is at volume. When a sigh signal is applied to line 425, AND gate 476 is disabled to prevent the passage of an output from comparator 470.

When a normal volume is to be delivered, line 425 will be high, by reason of the sigh volume flip flop 418 being reset, and this high signal will disable AND gate 478. However, the output of inverter 474 will be low, enabling AND gate 476 to permit passage of the output of comparator 470 so that when the cylinder has reached a normal volume, a low signal will be provided by OR gate 480 to produce the at volume signal on line 329.

Figure 13:
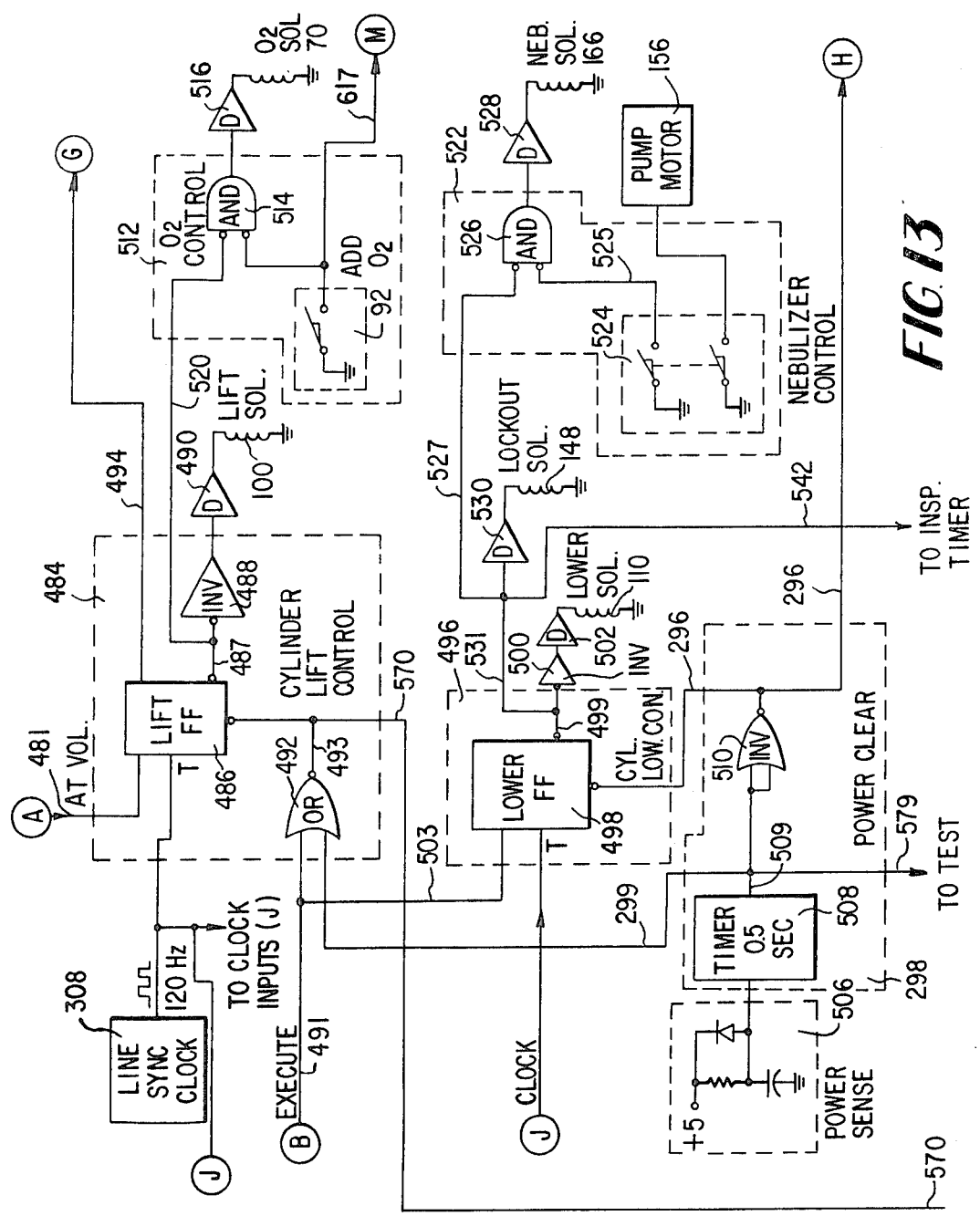

The cylinder lift control network is illustrated in FIG. 13 at 484. This network consists of a lift flip flop 486 which when set produces a low output on its line 487 which is fed through an inverter 488 and drive amplifier 490 to operate the lift solenoid 100. Energization of solenoid 100 opens the upper chamber of the cylinder to a source of vacuum, resulting in the raising, or lifting, of the piston formed by the weight 24 and the rolling diaphragm 18 to the desired volume height. The driver is turned on or off by the state of the lift flip flop 486. In the operation of the present respirator, the cylinder piston is to be returned to the desired volume level setting whenever the cylinder is not actually delivering air to the patient, i.e. in the absence of an execute cycle pulse. Therefore, when the cylinder is not at the desired volume, the cylinder volume control network 328 will produce a high signal at its output line 481, which signal is fed to the drive terminal of the flip flop 486. Accordingly the next line synchronizing pulse, produced by clock source 308, which is applied to the clock input of flip flop 486, will set the flip flop, resulting in a drive signal for the lift solenoid. The lift solenoid raises the cylinder weight until the volume control network is satisfied, at which time the signal on line 481 will shift to low and the next line synchronizing pulse applied to flip flop 486 will reset it, turning off the driver 490 and causing the lift solenoid valve to close.

During an execute cycle, when the cylinder piston is dropping below the preset volume value, the cylinder volume control will produce a high output, indicating that the preset conditions are not satisfied. To prevent the lift solenoid from being energized at this time, which would retard the lowering of the drive weight, the execute cycle signal from line 311 of the execute cycle control network 266 is applied by way of line 491 (terminal B) through an OR gate 492 and line 493 to inhibite lift flip flop 486 and prevent it from being set. OR gate 492 also receives the power on clear pulse from power clear network 298 by way of line 299 to make certain that the cylinder will not be told to lift during the start of machine operation. It will be noted that the lift flip flop 486 also produces an output signal on line 494 for other machine control use to be described. This signal is available at terminal point G.

Also illustrated in FIG. 13 is the cylinder lower control network 496 which includes a lower flipflop 498 having an output line 499 connected through an inverter 500 and a solenoid driver amplifier 502 to energize the lowering solenoid 110. When energized, the lower solenoid 110 operates its corresponding valve 108 (FIG. 1) to open the control chamber 26 of the cylinder to ambient pressure, allowing the cylinder to deliver air at a rate controlled by the flow rate setting. The lower flip flop 498 is activated by the presence of an execute pulse on line 491 which is applied to the setting input of flip flop 498 by way of line 503. When this signal is present, the next line synchronizing pulse from the system clock will set flip flop 498, resulting in a drive signal for the lower solenoid. When the end of the desired travel is reached, the execute cycle signal will drop low, and the next line synchronizing pulse will reset the lower flip flop 498. To prevent the cylinder from being lowered erroneously during power on, the flip flop is inhibited by the power clear pulse on line 296.

The power clearing network 298 is operative when power is first turned on in the machine. Since the several power supplies provided for this system take varying times to come up to full value, various transitory conditions occur within the control system. To prevent error in the initial machine operation which can occur, for example, if a transient signal should cause a flip flop circuit to set when it should not, the system is protected by the power clearing network. This network produces a power on clear pulse having a duration of one half second. When power is first turned on in the system, it is detected by the power sense network 506 which produces a trigger impulse to a timer 508. The timer produces a low level output signal for one half second on line 509, which signal is applied directly to selected flip flops in the system to hold them in their cleared state, or is first inverted by an inverter 510 and then applied to the desired clearing terminals. As the power supplies come up to full value, the power sensing network removes the control input to timer 508, allowing the timer to time out and shut off the signal on line 509, terminating the "power on" clear pulse.

To provide control of the oxygen supply valve 66, an oxygen control network 512 is provided. This control network consists of an AND gate 514 which produces an output to a solenoid driver 516 which in turn energizes the oxygen solenoid 70 to open solenoid valve 66. To energize the solenoid 70, the add oxygen switch 92, which is a control panel switch, must first be closed to enable the AND gate 514. The oxygen request signal is then gated by the output of lift flip flop 486 appearing on line 487, by way of line 520, whereby oxygen can be supplied to the cylinder only when the cylinder piston is being lifted. It should be noted that because the oxygen is mixed into the breathing gas only when the cylinder piston is being lifted, the mixing operation is totally independent of any patient parameters, for at this time the cylinder is blocked from the patient manifold. Accordingly, an accurately controllable percentage of oxygen can be obtained in the breathing gas through the use of a simple flow control valve in the oxygen supply line, limiting the need for the complex mixing valves required in prior devices.

A nebulizer control circuit 522 including a nebulizer selector switch 524, which is closed whenever the nebulizer is to be activated, is provided for controlling the operation of the respirator nebulizer. This switch is a double pole switch which activates the nebulizer pump 156 and which produces a signal on line 525 which enables an AND gate 526. Since the nebulizer is only to be operated during the lowering of the cylinder piston, the other input to AND gate 526 is obtained from the lower flipflop 498 by way of line 527. Therefore, when the cylinder is on its downstroke and the nebulizer switch is turned on, AND gate 526 produces an output which activates driver 528 and energizes solenoid 166.

Control of the inspiration lock out valve 124 is accomplished through a solenoid driver 530 which deenergizes the lock out solenoid 148 in response to a set output from the lower flipflop 498. The set output is applied to solenoid 148 by way of lines 499 and 531 so that valve solenoid 148 is energized all of the time that a breath is not to be delivered, and is released by the setting of flipflop 498 during a delivery mode.

Figure 14:
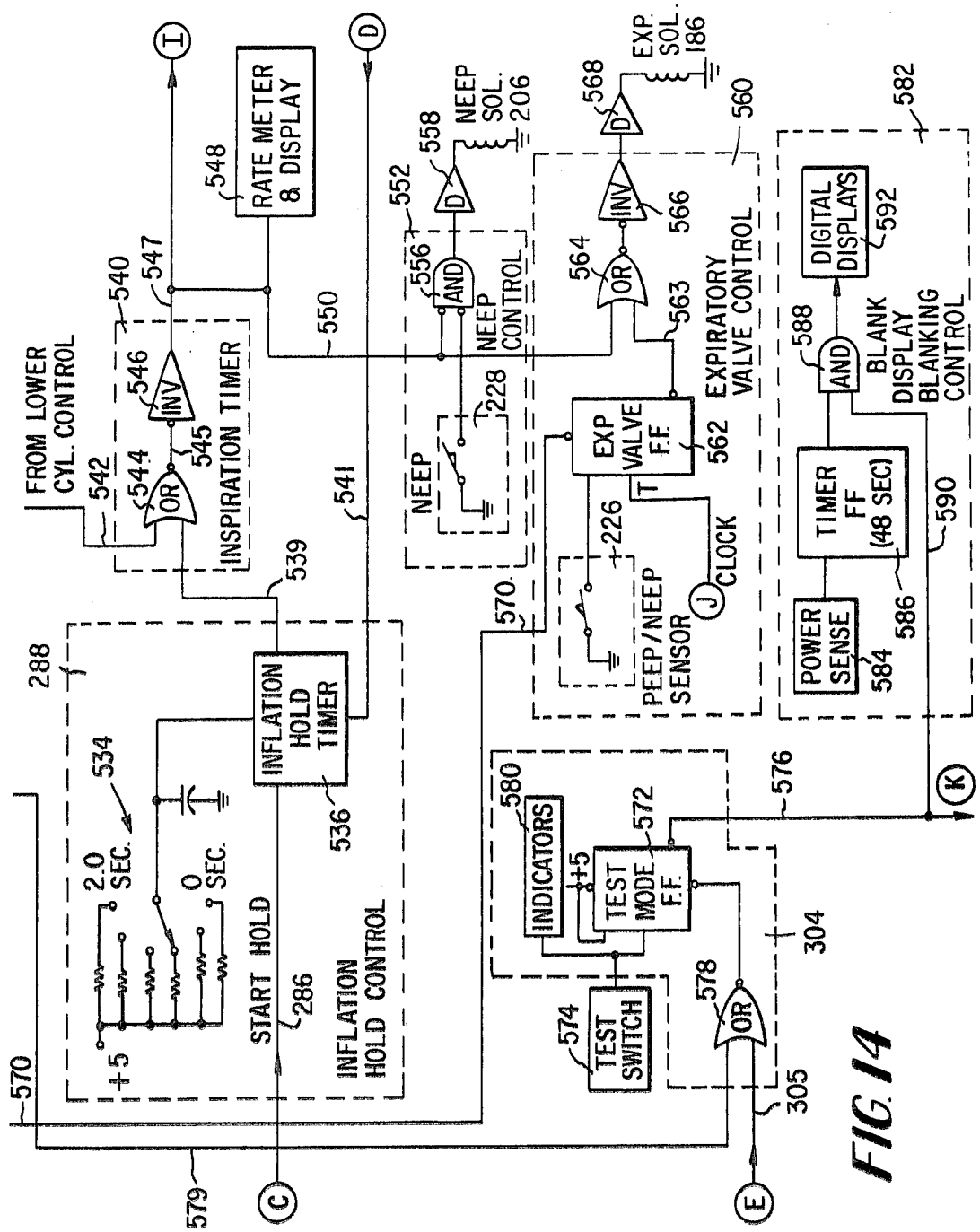

The inflation hold control network for the system is illustrated at 288 in FIG. 14. The hold control consists of a hold timer 536 which is initiated by the start hold signal provided on line 286 (terminal C) leading from the clear execute cycle network 260 (FIG. 10). This start hold signal initiates a time period which may be adjusted from 0.5ms to 2.0 seconds by means of a selector switch 538, the output of inflation hold timer 536 terminating when the timer 536 times out in accordance with the setting of selector switch 538.

The inflation hold timer 536 is adapted to be cleared by a ratio-error signal appearing on line 541 (terminal D) which will serve to stop the timer in the event of a ratio-error. The inflation hold is used to keep the air which has been delivered to the patient's lungs in the lungs for longer than the delivery time, allowing more time for gas transfer and lung pressure stabilization.

The output hold pulse from timer 536 continues for the length of the inflation hold, as set by selector 538, and is applied by way of line 539 to an inspiration timer 540. This timer also receives, by way of lines 499, 531 and 542, a pulse which corresponds to the set time of the cylinder lower flip flop 498. The two signals on lines 539 and 542 are applied to an OR gate 544 to produce a signal on line 545 which has a duration equal to the length of time of the cylinder downstroke plus the inflation hold time. This signal is inverted by inverter 546 and appears on output line 547 as the inspiration signal for the system. The inspiration signal is produced for each inspiration cycle of the machine and is available at terminal I to operate a ratemeter, generally indicated at 548, which is operative to produce a visual display of the average breathing cycle rate. A suitable rate meter for this purpose is illustrated and described in copending application Serial No. , of Theodore B. Eyrick and Neil R. Hattes, filed on even date herewith, entitled "Respiration Rate Meter", now U.S. Pat. No. 3,887,795 and assigned to the assignee of the present application.

The output from inspiration timer 540 applied by way of line 550 to a Neep control network 552. This control network is provided to enable a source of low vacuum to be applied cyclically to the expiration side of the patient manifold to assist in reducing pressure in the patient's lungs. The conditions of operation are that the Neep selector switch 228 be closed on the control panel of the respirator and that the machine be in the expiratory mode. The Neep switch 228 is connected to an AND gate 556, enabling the gate so that when a signal is received on 550 indicating the neither inhalation nor inflation hold is occurring a signal can be provided to the Neep solenoid 206 through a driver amplifier 558. Energization of solenoid 206 results in a pulse of pressure to the vacuum producing Venturi 198, as has been explained with respect to FIG. 2.

Control of the balloon valve 182 in the breathing manifold 138 (FIG. 2) is obtained by means of an expiratory valve control network 560 which includes an expiratory valve flip flop 562 to which is connected the Peep/Neep sensor switch 226. The output of flip flop 562 is connected by way of line 563 to an OR gate 564 which also receives the inspiration signal on line 550. The output of OR gate 564 is applied by way of inverter 566 to the drive amplifier 568 of the expiratory solenoid 186. The circuit is designed to operate the expiratory solenoid 186 when air is being delivered to the lungs, or to be held in the lungs, whereby ballon valve 182 will be expanded to prevent expiration.

Solenoid 186 is also to be operated when the preset Peep/Neep pressure is reached, as determined by the closure of sensor switch 226. When this set pressure is reached, the output from sensor 226 is low, and the next line synchronization pulse, which is applied to the timing, or clock input T of flipflop 562 will reset the flipflop and provide an output to OR gate 564, which will result in energizing the inspiration solenoid. When the pressure is not at the preset level, the sensor output from switch 226 will be high and the next line synchronizing pulse will set the flipflop, removing the input from OR gate 564 and deenergizing the solenoid.

The output of OR gate 492 in the cylinder lift control 484 (FIG. 13) responds to an execute cycle pulse or a clear pulse to produce a signal on line 570 which is applied to the direct set input of the flipflop 562. This flipflop is operated, however, so that the direct set input on line 570 will set the flipflop 562 to restore the expiratory control flipflop in preparation for next following expiration. The expiratory solenoid 186 is held energized during the delivery of air to the patient, by the inspiration signal on line 550.

A test mode flipflop 572 is provided in test mode network 304 to permit the system displays and indicators to be tested. In the test mode, the cylinder is lowered against a closed off cylinder outlet, or exit manifold, to permit checking for leaks and system compliance and also to verify that all display indicators and alarms are functioning. A test switch 574 on the control panel operates a latch to produce a clock pulse to the test mode flipflop 572. The flipflop produces a test mode level signal on output line 576 which is distributed to the system by way of terminal K to energize selected circuit elements for carrying out the test operation. The test mode flipflop 572 is cleared by means of a signal from OR gate 578 in response to a clear execute cycle pulse on line 305 (terminal E), which signal is produced when the cylinder has bottomed, as well as in response to a power clear signal from the power clear network 298, by way of line 579.

The output of the test switch 574 not only sets flipflop 572, but also energizes various indicator lamps 580 to indicate that a test is in progress.

The system incorporates a display blanking control network 582 which blanks the digital display of the system for a period of about 48 seconds after the power is turned on. The blanking control consists of a power sensing network 584, which senses the initial application of power to the system, and a power flipflop 586 which produces a 48 second high output pulse through an AND gate 588 to the digital displays 592 in the system to prevent them from turning on when the system is first turned on. However, if a test is occurring during that initial 48 second period, the test signal on line 576 will be applied through line 590 to disable gate 588 and allow the digital displays 592 to be turned on for test purposes.

Figure 15:
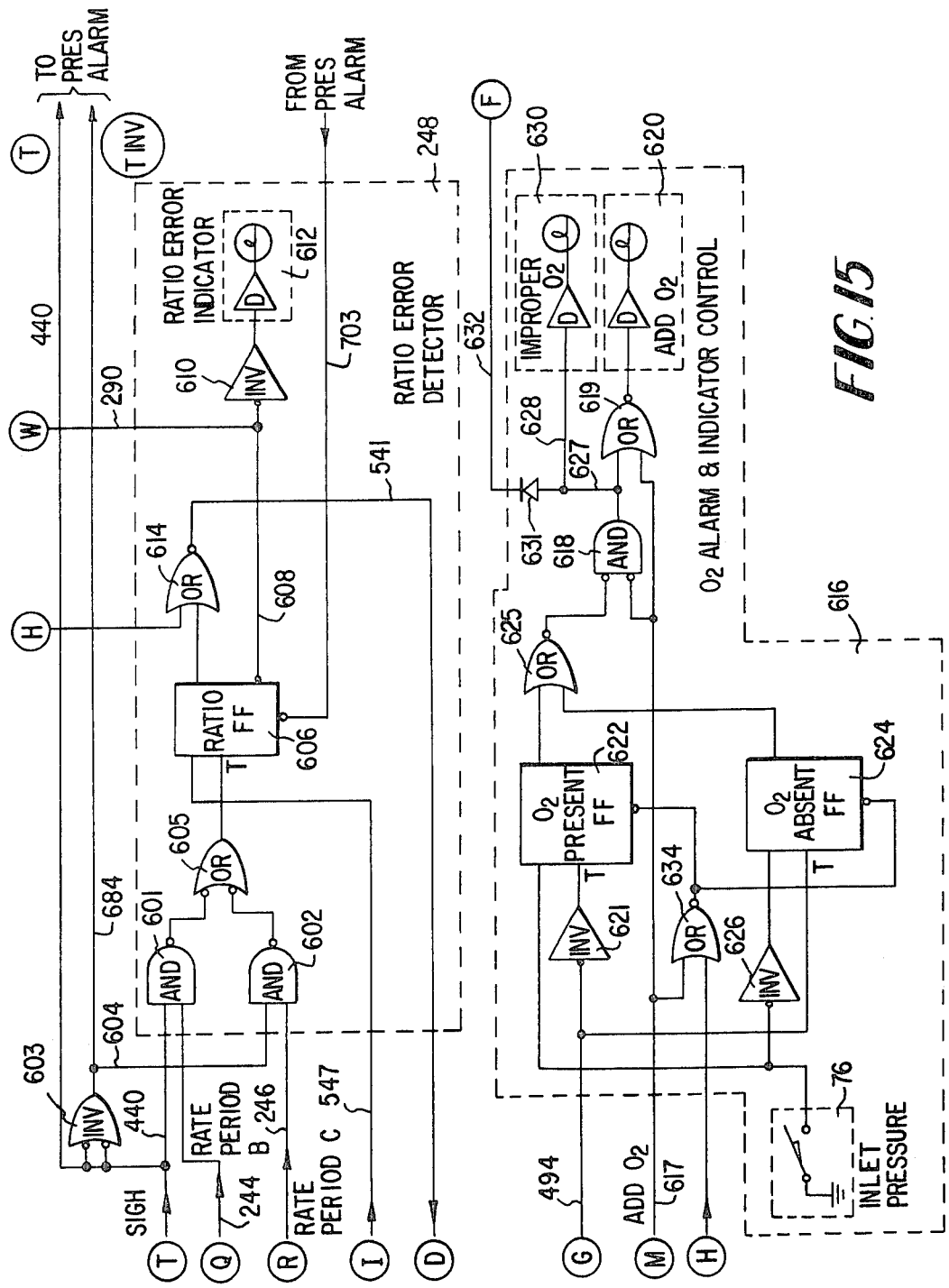

FIG. 15 illustrates the ratio-error alarm and detector network 248 which provides a visual alarm when the time of inspiration becomes longer than the time of expiration. The alarm also produces an aborting of the inspiration phase of machine cycling when an error occurs. The inflation hold time is defined as part of the inspiration, and its timer is also cleared when a ratio-error is detected during an inflation hold. Ratio-error is determined by using the pulses produced by the rate control network 230 and appearing on lines 244 and 246 (terminals Q and R), respectively, which define the first and the second halves of the breathing rate period. These pulses are applied to AND gates 601 and 602, respectively, in the error detector 248. The sigh signal appearing on line 440 (terminal T) is applied to AND gate 601, and the inverted sigh signal from inverter 603 is applied through line 604 to the AND gate 602. The outputs of AND gates 601 and 602 are fed through OR gate 605 to the clock input of a ratio flip flop 606. The ratio flip flop is driven by the inspiration signal appearing on line 547, which signal is the pulse derived from the inspiration timer 540 having a duration equal to the sum of the inhalation and inflation times.

The lead edge of the signal appearing on line 246 is that which results in initiation of the inspiration mode, or phase, of operation, while the signal appearing on line 244 occurs only during expiration; therefore, the signal on line 244 will be gone before the signal on line 246 appears. Accordingly, a high signal will appear on line 244 during the occurrence of a high signal on line 547 only if the inspiration time extends beyond the half way point of the breathing cycle. When this occurs, the output from AND gate 601 will be low, OR gate 605 will produce a high signal and the ratio flip flop will be clocked in the presence of the high signal on line 547. This will result in the setting of flip flop 606, producing an output on flip flop output line 608 which, after being inverted in inverter 610 will activate the ratio-error indicator lamp 612. This also produces a signal on line 290, leading to the clear execute cycle control 260 to produce a clearing output signal.

When the system is in a sigh mode, the signal appearing on line 440 is inverted and applied to AND gate 602, where it is gated with the signal appearing on line 246. This produces an output signal to OR gate 605 and the signal on line 246 is accordingly presented to the clock input of flip flop 606 prior to the occurrence of an inspiration signal on line 547. Therefore, there will not be an immediate sigh ratio-error. The next occurrence of a high signal on line 246 will be one entire normal rate cycle later and at this time if the inspiration signal is still present flip flop 606 will be set to produce a ratio-error alarm. The signal for clearing the inflation hold control 288 is provided by ratio flip flop 606 during an alarm mode by way of OR gate 614 and line 541 (terminal D). The power on clear signal (Terminal H) is also gated to the hold control 288 by way of OR gate 614.

An oxygen alarm and indicator control network 616 is provided to monitor the presence of oxygen at a time when oxygen is to be present, and to verify that there is none between the cylinder filling cycles. This produces a comprehensive alarm that checks both the oxygen source and the oxygen control system.

Oxygen is called for in the system by rotating the oxygen add control 90 (FIG. 1) from its 21 percent position, thereby activating the add oxygen switch 92 (FIG. 13) to produce an input signal on line 617 (terminal M). This signal is applied to an AND gate 618 and to an OR gate 619, enabling both gates. Because initially there is no alarm condition, both inputs to the OR gate 619 are low and its output high to activate the add oxygen display lamp 620. A cylinder lift signal from line 494 (terminal G) is applied to the control network 616 through inverter 621 to drive the clock input of an oxygen present flip flop 622 when the cylinder has finished lifting. The signal is also applied to the clock input of an oxygen absent flip flop 624 to drive that flip flop when the cylinder lift signal starts. The inlet pressure switch 76 produces an output which is applied directly to the oxygen present flip flop 622 and through an inverter 626 to oxygen absent flip flop 624. If the desired inlet pressure has been reached by the time the cylinder has finished lifting, flip flop 622 is driven to a reset state, indicating a nonalarm status. However, if pressure is not reached by the end of cylinder lifting, flip flop 624 is clocked to a set state, producing a signal which passes through OR gate 625, AND gate 618, and lines 627 and 628 to activate the "improper oxygen" indicator lamp 630. This signal is also applied through diode 631 and line 632 to the audible alarm 456. In addition, the add oxygen lamp 620 is turned off.

A failure of the control system to shut off the oxygen supply at other than the cylinder lift time will result in a continuous actuation of the oxygen pressure switch 76, with the resultant alarm condition. To allow maximum time for the pressure in the supply conduit 74 to bleed down to a lower value between supply cycles, the switch level is checked at the moment the cylinder is told to lift. If the switch is deactivated at lift time, flip-flop 624 is clocked to a reset state, indicating a nonalarm mode. However, if the switch 79 is activated at this time, indicating a high pressure remaining in conduit 74, flipflop 622 is clocked by the signal on line 494 to a set state, and the output passes through OR gate 625 to initiate the alarm in the manner previously described.

The alarm may be reset by a power clear signal, by turning off the add oxygen switch, which direct clears flip flops 622 and 624 through OR gate 634, or by restoration of the nonalarm condition.

FIG. 16 illustrates an improper cycle alarm network 640 which functions as the watch dog alarm of the system. This network sounds an alarm if the cylinder has not completed a full stroke for a period of 20 seconds after the last full stroke has been completed. The alarm is independent of the rest of the control system in that it generates its own power clear pulse, shares no logic circuits with the rest of the system and is isolated from the low pressure alarm by means of diodes. Further, the alarm is provided with its own tracking components to detect the operation of the cylinder, with a bottom sensing switch 276 and a top sensing switch 642 being provided to monitor the end points of travel of the cylinder. Although it is preferred that the switches be separate from the normal system control sensors, it will be apparent that if desired they can be a part of the cylinder follower mechanism illustrated in FIG. 1.

When the power is turned on in the system, a power sense network 644 generates a clearing pulse which resets flip flop 646. This flip flop may also be reset by closure of the manual reset switch 460 which may be located on the respirator control panel. When flip flop 646 is clear, it directly clears a 20 second timer 648 by way of an OR gate 650. After the power clear or reset operation has taken place, the first time that the cylinder goes through its bottom position, a low signal is produced by the bottom switch 276 which is fed through inverter 652 and AND gate 654 to trigger a one-shot multivibrator 656. Circuit element 656 produces an output pulse which is applied by way of line 657 to clock set flip flop 646, releasing its inhibit, or clearing, hold on timer 648. However, the timer will be held cleared by the pulse duration of the output from the multivibrator 656 which is applied by way of line 658 and OR gate 650 to the timer clearing terminal. As, as soon as the pulse from the one-shot multivibrator terminates, the timer begins a 20 second time out. If the cylinder cycles through the bottom position prior to the timing out of timer 648, the one-shot multivibrator will be re-pulsed, and the timer cleared.

The output of OR gate 650 is also connected to a flip flop 660 which is connected to receive an output pulse from timer 648, by way of an inverter 662 and line 663, so that if the timer times out, flip flip 660 will be set to activate an "improper cycle" indicator 664 by way of an inverter 666. However, if the timer is terminated by an output from the one-shot multivibrator 656, flip flop 660 will not be set. If the timer 648 completes its time out without the occurrence of a signal from the one-shot multivibrator, flip flop 660 will illuminate improper cycle lamp 664, and at the same time produce a high output on line 668 which is fed through a diode 669 and a line 670 to the audible alarm 456.

One additional condition will trip the improper cycle alarm. The photoelectric top sensing switch 642 is normally positioned beyond the maximum volume position of the cylinder, and can be actuated only if by an error in the system the cylinder is lifted beyond any possible set position. This will produce a signal through inverter 672 which will direct set the alarm by way of line 673, and this signal will prevent the alarm from being reset as long as the cylinder is stuck at the top.

Figure 17:
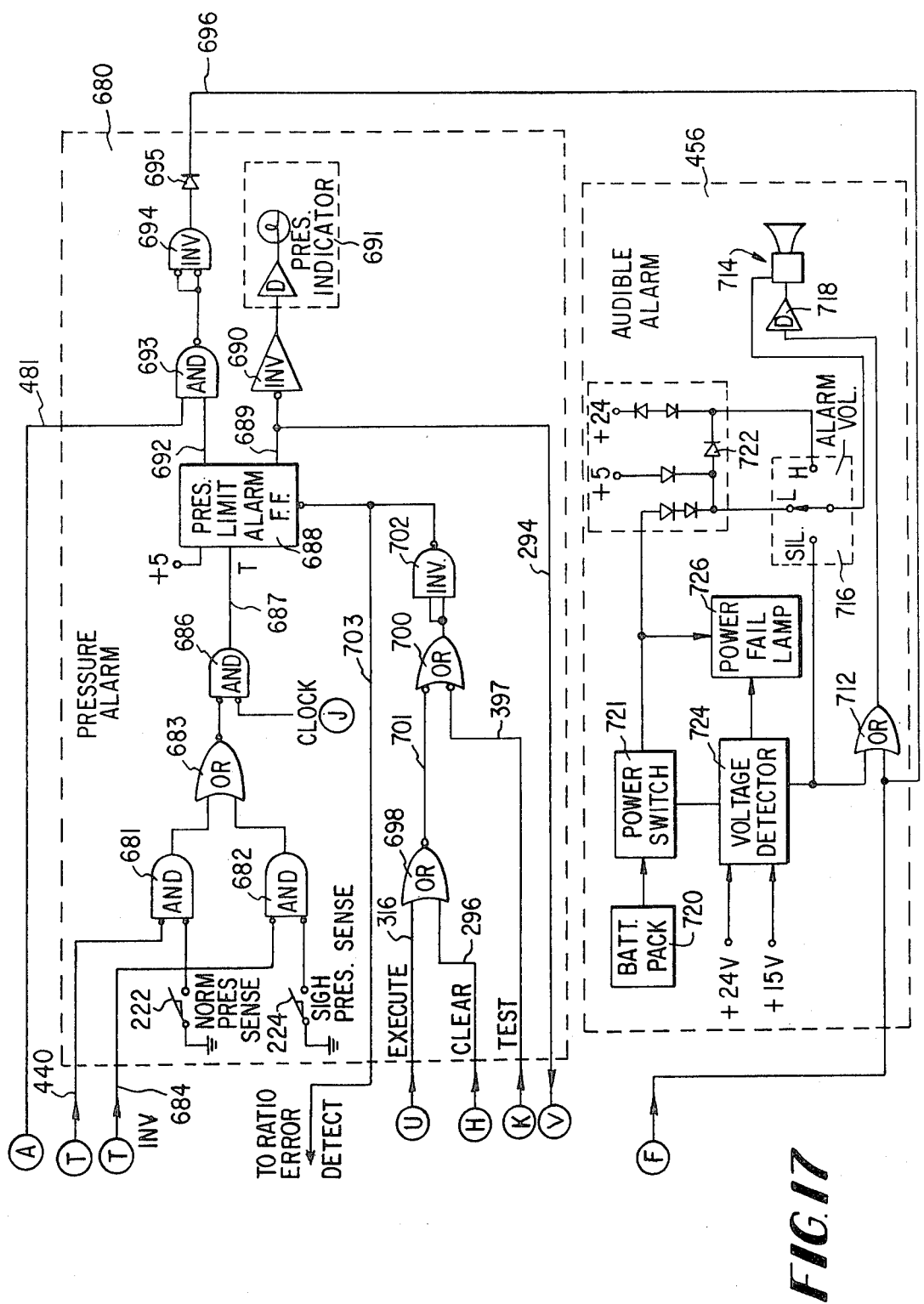

The pressure alarm network illustrated in FIG. 17 at 680 is provided to indicate that the pressure at the patient manifold has reached the desired limit, as set by the operator on a control panel by either the normal pressure limit selector or the sigh pressure limit selector. As a further safeguard, the remainder of the cylinder delivery stroke is aborted when the pressure limit is reached in order to prevent additional increase in pressure. Pressure limits are sensed by the photoelectric gauge switches 222 and 224. They provide a low output when the manifold pressure matches the set pressure. AND gates 681 and 682 and OR gate 683 cooperate to act as a two input selector switch that gates through the outputs of either the normal pressure sensing switch 222 or the sigh pressure sensing switch 224, depending on whether the machine is in a normal or sigh cycle, as defined by the level of the sigh input signal appearing on line 440 or as inverted by inverter 603 (FIG. 15) and appearing on line 684. The selected signal is gated through AND gate 686 by the 120 Hz clock to provide an output pulse on line 687 when a pressure limit has been reached. This pulse is applied to the clock input T of a pressure alarm flip flop 688 which is driven to a set state, producing an output on line 689 which is inverted by inverter 690 to operate a pressure indicator lamp 691. The signal appearing on line 689 is also applied by way of line 294 (terminal V) to the clear execute cycle network 260 to produce a clearing pulse whereby the delivery stroke is aborted. Output 692 of the flip flop 688 is gated with the at volume signal appearing on line 481 (terminal A) by AND gate 693 for application to an inverter 694. The resultant signal is applied through a diode 695 and line 696 to the audible alarm network 456 to provide an audible alarm for the time that it takes the aborted cylinder stroke to recover to set volume. This momentary alarm is to call attention to the fact that a pressure limit was reached.

The pressure limit alarm flip flop 688 is cleared by a network consisting of an OR gate 698 receiving an execute signal from line 316 or a power clear signal from line 296, with the output of gate 698 being applied to a second OR gate 700 by way of line 701. Also applied to OR gate 700 is the test signal from line 397 (terminal K), with the output of OR gate 700 being inverted by inverter 702 to clear the pressure limit alarm. The composite signal provided by inverter 702 may also be used to clear and reset the ratio-error detector network by way of line 703. The inclusion of the test input prevents the two alarms from activating during a test cycle, and thus prevents the alarm system from producing an undesired aborting of the test operation.

The audible alarm network 456 receives alarm input signals by way of lines 632, 696, 670, and 710 (terminal F) which signals are applied through an OR gate 712 to a suitable sound generator such as a Mallory Sonalert model 7C628, generally indicated at 714. The loudness of the alarm is controlled by a volume selector switch 716 which varies the magnitude of the voltage applied to the Sonalert driver amplifier 718. To insure that the alarm will still sound in the event of a failure of the 5 volt power supply, a battery pack 720 is provided. When the power switch 721 is closed, the system will operate from the power supply rather than the battery pack until such time as the supply fails.

The operation of the high alarm is provided by a 24 volt supply fed through a zener diode. In the event of a failure of the 24 volt supply, the 5 volt supply plus the battery pack supply will be sufficient to activate the alarm through a connecting diode 722. Thus, if a power failure takes place in either the high or low mode, the alarm is powered by whichever power supply is not affected.

The alarm may be set to a silent mode, in which case there will be an audible alarm only in the event of a power failure, at which time the power fail alarm will be powered through the voltage detector 724. If a power failure is sensed by detector 724, a power fail lamp 726 will be illuminated and the audible alarm will sound.

Thus, there has been provided a respirator system which operates in an accurate and efficient manner to provide a flexible method of controlling the breathing cycle of a patient. Although the present invention has been described in terms of a preferred embodiment, it will be apparent to those skilled in the art that numerous variations and modifications can be made without departing from the true spirit and scope of the invention as set forth in following claims.

What is claimed is:

1. In a respirator system, the method of delivering a variable but selectable volume of breathing gas at a preselected limited rate, comprising:
   mounting a gravity-operated driver for vertical motion within a closed housing;
   defining within said housing an upper control chamber above said driver and a lower delivery chamber below said driver, said chambers being divided by a diaphragm connected between said driver and said housing;
   producing a vacuum within said control chamber to lift said driver and thereby expand said delivery chamber;
   controlling said vacuum to regulate the distance and the rate at which said driver is lifted to expand said delivery chamber to a selected volume;
   admitting breathing gas at substantially atmospheric pressure to said delivery chamber only during the lifting of said driver;
   releasing said vacuum at a controlled and variable rate to enable said driver to fall solely under the force of gravity at a maximum rate determined by the rate of release of said vacuum to contract said delivery chamber;
   discharging said breathing gas from said delivery chamber at a rate and pressure limited by the rate of release of said vacuum and the weight of said driver; and
   periodically and alternately producing and releasing said vacuum for drawing in and discharging breathing gas in a breathing cycle.

2. The method of claim 1, wherein the step of controlling said vacuum includes selectively operating a control valve connected between a source of vacuum and said control chamber to lift said driver a variable but selectable and predeterminable distance to expand the delivery chamber to a selectable volume, whereby a selectable maximum volume of breathing gas is available in said discharge chamber upon release of said vacuum.

3. The method of claim 2, wherein the step of releasing said vacuum comprises selectively and controllably opening a bleeder valve connected between said control chamber and atmosphere to admit air at atmospheric pressure to said control chamber at a predetermined, variable, but limited rate to enable said driver to discharge the selected volume of breathing gas available in said discharge chamber.

4. The method of claim 3, further including:
   connecting at least one source of breathing gas to said delivery chamber; and
   controlling the flow of breathing gas from said source to said delivery chamber.

5. The method of claim 4, wherein the step of controlling said source of breathing gas includes selectively and controllably opening a gas supply valve to allow breathing gas under pressure to flow at a limited rate and under limited pressure to said delivery chamber only during the lifting of said driver.

6. The method of claim 5, further including connecting two sources of breathing gas to said delivery chamber, said step of controlling the flow of breathing gas including regulating the relative rates of flow of breathing gas from each of said two sources to produce a selectable mixture of breathing gases in said delivery chamber.

7. The method of claim 1, wherein the step of controlling said vacuum in said control chamber includes selectively operating a control valve to correct a source of vacuum to said control chamber for a variable, preselected period of time to lift said driver a distance dependent upon said period of time to expand said delivery chamber to a variable preselected volume.

* * * * *